US006251884B1

(12) United States Patent
Setchell

(10) Patent No.: US 6,251,884 B1
(45) Date of Patent: Jun. 26, 2001

(54) SULFATE CONJUGATES OF URSODEOXYCHOLIC ACID, AND THEIR BENEFICIAL USE IN INFLAMMATORY DISORDERS AND OTHER APPLICATIONS

(75) Inventor: Kenneth D. R. Setchell, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

(21) Appl. No.: 09/028,036

(22) Filed: Feb. 24, 1998

Related U.S. Application Data

(62) Division of application No. 08/560,992, filed on Nov. 21, 1995, now Pat. No. 5,763,435.

(51) Int. Cl.$^7$ .................................................. A61K 31/56
(52) U.S. Cl. .................................. 514/182; 514/169
(58) Field of Search ...................... 514/169, 182

(56) References Cited

U.S. PATENT DOCUMENTS

| 4,565,811 | 1/1986 | Di Schiena | 514/182 |
| 5,460,812 | 10/1995 | Sipos | 424/94.1 |

FOREIGN PATENT DOCUMENTS 0117570 9/1984 (EP) .

OTHER PUBLICATIONS

Hcaplus, DN 124:193196, Rodrigues et al., Gastroenterology, 109(6), 1835–44, 1995.*
Hcaplus DN 108:204872, Bandiera et al., Synth. Commun., 17(9), 1111–17, 1987.*
Hcaplus DN 93:109921, Goto et al., J. Liq. Chromatogr., 3(5), 645–55, 1980.*
Czygan, P., et al., *Chenodeoxycholic acid but not ursodeoxycholic acid enhances colonic carcinogenesis in the rat*, Falk Symposium 33, pp. 393–395, 1982.
Earnest, D. L., et al., *Chemoprevention of Azoxymethane–induced Colonic Carcinogenesis by Supplemental Dietary Ursodeoxycholic Acid*, Cancer Research, pp. 5071–5074, Oct. 1, 1994.
Franzone, J. S., et al., *Attivita farmacologica dell'acido ursulcolico, forma solubilie dell'UDCA*, Boll. Chim. Farm., vol. 126, No. 7, 1987, pp. 282–288, XP000644486.
Franzone, J. S., et al., *Farmacocinetica e metabolism epatico dell'acido ursulcolico (forma solubile dell'UDCA) nel ratto*, Boll. Chim. Farm. vol. 126, No. 7 1987, pp. 289–293, XP000644487.
Goto, J., et al., *Synthesis of Monosulfates of Unconjugated and Conjugated Bile Acids*, Chem. Pharm. Bull., vol. 27, pp. 1042–1411, 1979.
Pacini, N., et al., *Transformation of Sulfated Bile Acids by Human Intestinal Microflora*, Arzneimittelforschung, vol. 37, No. 8, Aug. 1987, pp. 983–987, XP000647307.

Rigas, B., et al., Abstract, *Ursodeoxycholic Acid and Piroxicam Up–Regulate MHC Antigen Expression in Rat Coloncytes During Colon Cancer Development*, Gastrointestinal Oncology, A433, Apr. 1994.
Roda, A., et al., *Improved Intestinal Absorption of an Enteric–Coated Sodium Ursodeoxycholate Formulation*, Pharmaceutical Research, vol. 11, No. 5, May 1994, pp. 642–647, XP000645007.
Sano, N., et al., *Estradiol–17beta–glucuronide–induced cholestasis*, Journal of Hepatology, vol. 17, No. 2, Feb. 1993, pp. 241–246, XP000645240.
Setchell, K. D. R., et al., Abstract, *A Simple, Rapid and Non–Invasive Test of Compliance . . . Urinary Metabolite*, AASLD Abstracts of Papers, No. 855, 1991.
Takikawa, H., et al., *Effects of organic anions and bile acids on biliary lipid excretion in hyperbilirubinemic mutant Sprague–Dawley rats*, Journal of Hepatology, vol. 17, No. 2, 1993, pp. 247–252, XP002030420.
Takikawa, H., et al., *Effects of ursodeoxycholate, its glucuronide and disulfate and beta–muricholate on biliary bicarbonate concentration and biliary lipid excretion*, Journal of Hepatology, vol. 15, No. 1–2, May 1992, pp. 77–84, XP002030420.

* cited by examiner

Primary Examiner—Dwayne C. Jones
Assistant Examiner—C. Delacroix-Muirheid
(74) Attorney, Agent, or Firm—Wood, Herron & Evans, L.L.P.

(57) ABSTRACT

One aspect of this invention is directed to a pharmacologically acceptable composition including a sulfate of 3 alpha, 7 beta-dihydroxy-5 beta-cholan-24-oic acid (Ursodeoxycholic acid or "UDCA") and a pharmacologically acceptable carrier. In a preferred composition, the sulfate is UDCA-3-sulfate, UDCA-7-sulfate, UDCA-3,7-disulfate, glyco-UDCA-3-sulfate, glyco-UDCA-7-sulfate, glyco-UDCA-3,7-disulfate, tauro-UDCA-3-sulfate, tauro-UDCA-7-sulfate, tauro-UDCA-3,7-disulfate or a combinations thereof. Another aspect of the invention concerns a method of delivering UDCA to a mammal to inhibit or treat a disorder, which includes administering a sulfate of UDCA to the mammal in an amount sufficient to inhibit or treat the disorder. For example, a UDCA sulfate may be used to advantage in inhibiting or treating an inflammatory condition of the gastrointestinal tract, such as colon cancer, rectum cancer, a neoplasm of the colon, a neoplasm of the rectum, carcinogenesis of the colon, carcinogenesis of the rectum, ulcerative colitis, an adenomatous polyp, familial polyposis and the like. A sulfate of UDCA also may be administered to inhibit or treat an inflammatory disorder of the liver. A UDCA sulfate may be used to improve serum biochemistries of liver disease or liver function, to increase bile flow or to decrease biliary secretion of phospholipid or cholesterol. In yet a further aspect, the invention is directed to a method of maintaining an isolated organ by perfusing the organ with a sulfate of UDCA.

22 Claims, 11 Drawing Sheets

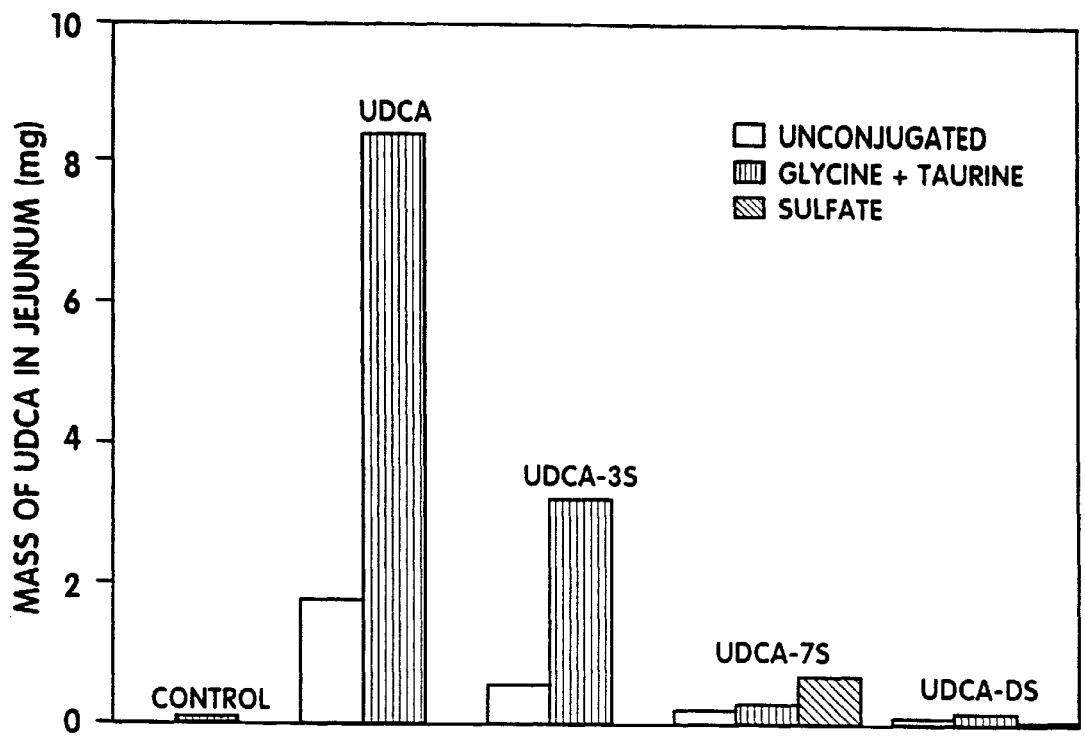
FIG. IA
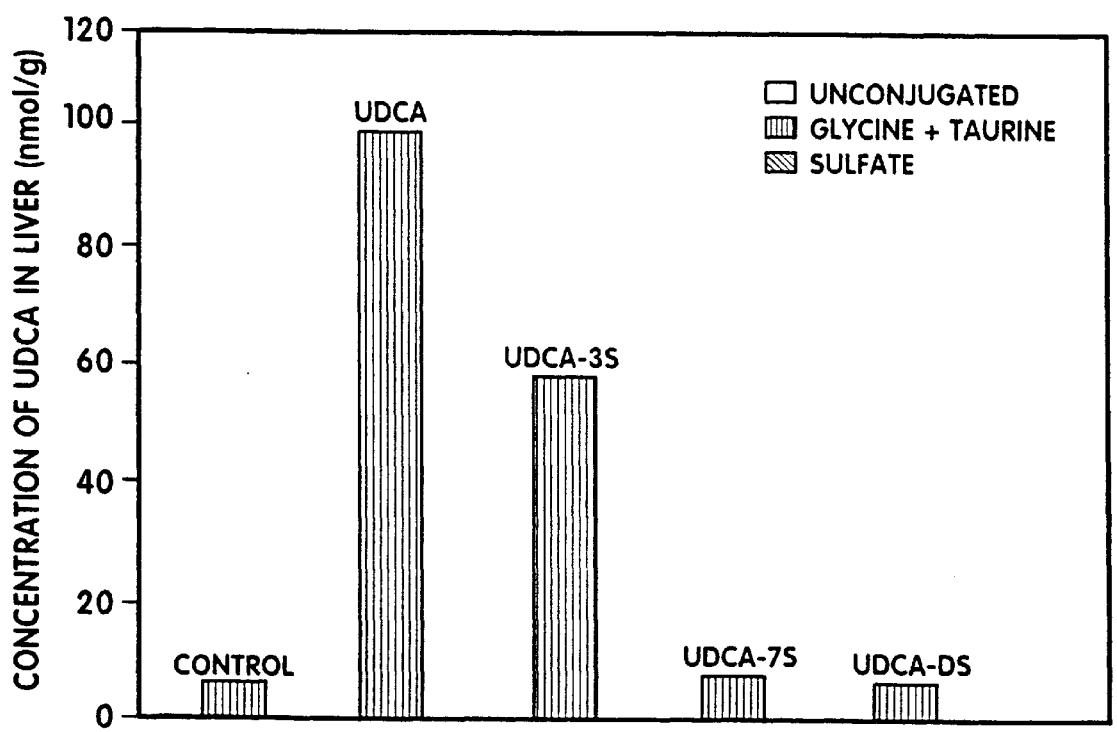
FIG. IB

SULFATE CONJUGATES OF URSODEOXYCHOLIC ACID, AND THEIR BENEFICIAL USE IN INFLAMMATORY DISORDERS AND OTHER APPLICATIONS

This is a division, of application Ser. No. 08/560,992, filed Nov. 21, 1995, now U.S. Pat. No. 5,763,435.

BACKGROUND OF THE INVENTION 3 alpha, 7 beta-dihydroxy-5 beta-cholan-24-oic acid ("Ursodeoxycholic acid" or "UDCA") has been used clinically for more than two decades, initially proving effective for the treatment of patients with cholelithiasis and more recently showing promise in the treatment of patients with cholestatic liver diseases. It is well established that oral administration of UDCA leads to a significant improvement in serum liver enzymes, and based on results from long-term clinical trials, the consensus opinion is that UDCA is beneficial for the treatment of early-stage primary biliary cirrhosis. In addition, clinical trials have shown that UDCA is beneficial in improving clinical and biochemical indices of hepatic function in patients with sclerosing cholangitis, cystic fibrosis and chronic hepatitis.

Despite the promising effects shown by UDCA in liver diseases, the exact mechanism of its action remains unclear. Early speculation suggested that a shift in the hydrophobic/hydrophilic balance of the biliary bile acid pool was an important determinant of its effectiveness, but recent data do not totally support this contention; and the improvement in liver function is almost certainly the result of a marked hypercholeresis induced by UDCA, which facilitates the biliary excretion of potentially more toxic bile acids or other endogenous agents.

In studies focussing on the metabolism of UDCA in patients with a variety of liver diseases, the appearance of substantial amounts of the C-3 sulfate ester of UDCA in the urine has been consistently observed, and this specific metabolite has proven to be a useful marker for UDCA compliance. In addition, animal studies have suggested that sulfation of bile acids may represent an important metabolic pathway for preventing cholestasis and limiting hepatocellular damage.

The cytotoxic or membrane-damaging effect of a bile acid is related to its physicochemical properties. Hydrophobic bile acids are markedly more membrane damaging than hydrophilic bile acids, and relative indices of cytotoxicity have been established based on the retention volume of the bile acid in reverse-phase high-pressure liquid chromatography systems or from partition coefficients in octanol/water. It is paradoxical that the human liver synthesizes chenodeoxycholic acid, a hydrophobic molecule that is intrinsically hepatotoxic, as one of its primary bile acids; in cholestasis, the hepatic accumulation of this bile acid may initiate, contribute to, or exacerbate liver damage. In contrast, UDCA, the 7β-epimer of chenodeoxycholic acid, is highly hydrophilic and has been shown to counteract the membrane-damaging effects of hydrophobic bile acids. This is one rationale for the therapeutic use of UDCA in the treatment of a variety of liver diseases. After the oral or intravenous administration of UDCA, this bile acid is efficiently biotransformed in the liver, mainly by conjugation. Negligible concentrations and proportions of unconjugated UDCA are consequently found in human bile, even after the administration of relatively high doses.

UDCA also may have a therapeutic role beyond its use in the treatment of various liver diseases. In this respect, data are emerging from animal models of colonic carcinogenesis that suggest a protective role for UDCA.

However, actual delivery of UDCA to the colon is problematic, in that, at the usual therapeutic doses administered orally (10–15 mg/kg body weight/day), UDCA is relatively well absorbed from the intestine and efficiently biotransformed in the liver mainly by conjugation. As a consequence, it is extremely difficult to deliver effective amounts of UDCA specifically to the colon.

Therefore, given this limitation of delivery to the colon, it would be extremely beneficial to have a compound, composition or method in which UDCA may be effectively delivered to the colon. It also would be desirable to have a compound, composition or method which may be used to deliver UDCA effectively to other portions of the gastrointestinal tract. In addition, it would be advantageous to have a compound, composition or method for use in effectively inhibiting or treating an inflammatory disorder of the gastrointestinal tract or liver.

SUMMARY OF THE INVENTION

One aspect of this invention is directed to a pharmacologically acceptable composition including a sulfate of 3 alpha, 7 beta-dihydroxy-5 beta-cholan-24-oic acid (Ursodeoxycholic acid or "UDCA") and a pharmacologically acceptable carrier. In a preferred composition, the sulfate is UDCA-3-sulfate, UDCA-7-sulfate, UDCA-3,7-disulfate, glyco-UDCA-3-sulfate, glyco-UDCA-7-sulfate, glyco-UDCA-3,7-disulfate, tauro-UDCA-3-sulfate, tauro-UDCA-7-sulfate, tauro-UDCA-3,7-disulfate or a combinations thereof.

Another aspect of the invention concerns a method of delivering UDCA to a mammal to inhibit or treat a disorder, which includes administering a sulfate of UDCA to the mammal in an amount sufficient to inhibit or treat the disorder. For example, a UDCA sulfate may be used to advantage in inhibiting or treating an inflammatory condition of the gastrointestinal tract, such as colon cancer, rectum cancer, a neoplasm of the colon, a neoplasm of the rectum, carcinogenesis of the colon, carcinogenesis of the rectum, ulcerative colitis, an adenomatous polyp, familial polyposis and the like. A sulfate of UDCA also may be administered to inhibit or treat an inflammatory disorder of the liver. A UDCA sulfate may be used to improve serum biochemistries of liver disease or liver function, to increase bile flow or to decrease binary secretion of phospholipid or cholesterol.

In yet a further aspect, the invention is directed to a method of maintaining an isolated organ by perfusing the organ with a sulfate of UDCA.

This invention offers several benefits and advantages over the prior art. For example, therapeutically effective quantities of UDCA may be delivered to the colon and other portions of the gastrointestinal tract for inhibition or treatment of inflammatory disorders, such as colon cancer and the like. In addition, sulfates of UDCA may be used effectively to inhibit or treat liver disease or improve liver function. These and other benefits and advantages will become readily apparent to one of ordinary skill in the art upon review of the following detailed description of the invention.

BRIEF DESCRIPTION OF THE DRAWINGS

FIGS. 1A and 1B show a comparison of the total mass of UDCA in the entire jejunum (FIG. 1A) and concentration in liver tissue in control rats (FIG. 1B) after oral administration of UDCA, UDCA-3S, UDCA-7S and UDCA-DS. Bile acids were separated according to their mode of conjugation by anion-exchange chromatography before analysis of the individual fractions using GC-MS. Results are expressed as the mean values of all animals;

DETAILED DESCRIPTION OF THE INVENTION

Figure 2:
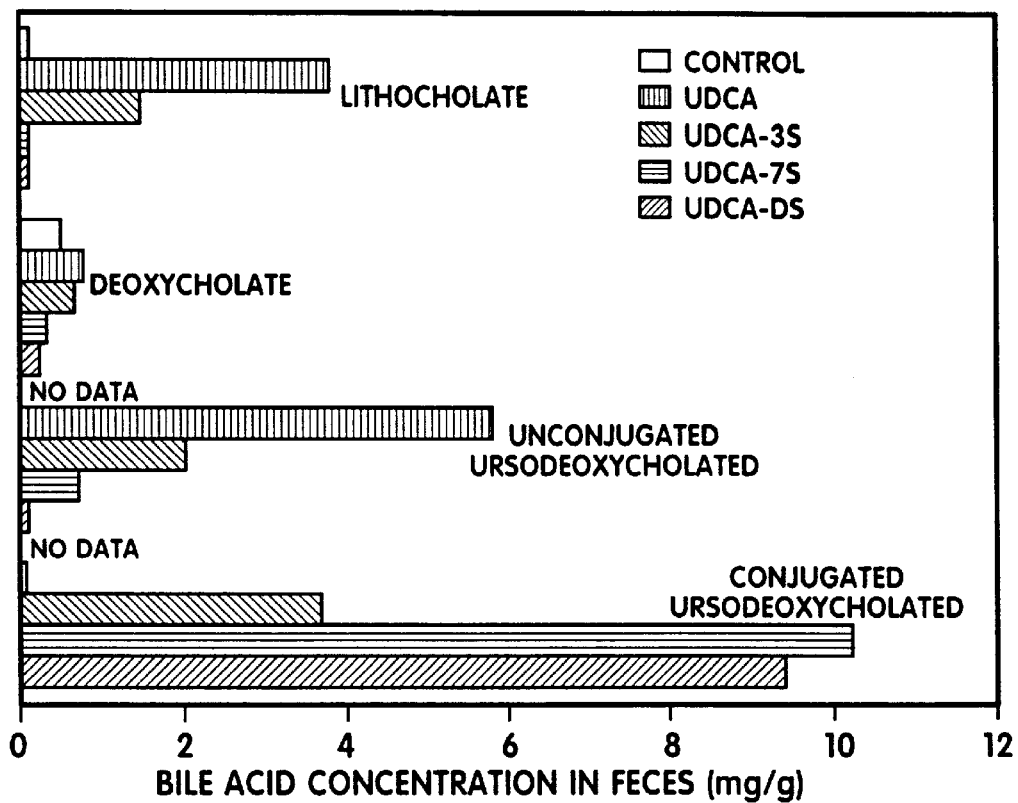
FIG. 2 shows fecal bile acid excretion in control rats and rats orally administered UDCA, UDCA 3-S, UDCA 7-S and UDCA-DS. Bile acids were separated according to their mode of conjugation by anion-exchange chromatography before analysis of the individual fractions using GC-MS. Results are expressed as mean values of all animals.

Additional abbreviations appearing below include: GC (gas-liquid chromatography), GC-MS (gas-liquid chromatography mass spectrometry), FAB-MS (fast atom bombardment-mass spectrometry), TLC (thin layer chromatography), HPLC (high-performance liquid chromatography), UDCA-3S (ursodeoxycholic acid 3-sulfate), UDCA-7S (ursodeoxycholic acid 7-sulfate), UDCA-DS (ursodeoxycholic acid 3, 7-disulfate), tBDMS ether (tert-butyldimethylsilyl ether) and tBDMC (tert-butyldimethylsilyl chloride).

The data presented below compare the intestinal metabolism and behavior of the individual bile acid sulfates of UDCA with the unconjugated bile acid and show, among other things, that the presence of the C-7 sulfate moiety protects against bacterial degradation and inhibits intestinal absorption of UDCA.

MATERIALS AND METHODS

Synthesis of Sulfated Esters of UDCA

UDCA, 99% pure, was obtained from Sigma Chemical Co. (St. Louis, Mo.). The monosulfate and disulfate esters of UDCA were prepared by the methods described in step-by-step detail later on in this detailed description. In brief, the synthesis of the monosulfate esters involved selective protection of each of the ring hydroxyl groups in the UDCA molecule, followed by sulfation of the unprotected hydroxyl group and hydrolysis of the protecting group to release the monosulfate ester. The disulfate conjugate of UDCA was prepared by the reaction of UDCA with chlorosulfonic acid. Gas chromatography - mass spectrometry (GC-MS) was used to confirm the position of the sulfate groups by analysis of the products after oxidation, solvolysis, and conversion to methyl/ester-trimethylsiyl ether derivatives. Chromatographic purity of the synthetic bile salts was found to be >97% for UDCA 7-sulfate and UDCA 3,7-disulfate and >95% for UDCA 3-sulfate, as determined by high-pressure liquid chromatography, thin-layer chromatography, and capillary-column gas chromatography.

ANIMAL STUDIES

Male Sprague-Dawley rats (Harlan Sprague-Dawley, Inc., Indianapolis, Ind.), weighing 210–290 g, were maintained on a 12-hour light-dark cycle and fed standard laboratory chow ad libitum for 3 days. The animals were then transferred to metabolic cages in which they were housed individually and fed the same diet. UDCA, UDCA 3-sulfate, UDCA 7-sulfate, and UDCA 3,7-disulfate were administered by gavage at a dose of 250 mg/day for 4 consecutive days. Each group comprised 3–6 rats. Body weights of the animals were measured each day. On day 5, the animals killed were by exsanguination under ether anesthesia. Plasma was collected and frozen at −20° C. The liver was removed, rinsed in normal saline, and flash-frozen in liquid nitrogen. Urine and feces were collected every 24 hours and frozen at −20° C. All animals received humane care in compliance with the "Guide for the Care and Use of Laboratory Animals" prepared by the National Academy of Sciences (National Institutes of Health publication no. 86–23, revised in 1985).

BILE ACID ANALYSIS

Unconjugated and Sulfate Bile Acids in Intestinal Contents and Feces

Intestinal contents were weighed and dissected into small pieces. In each group, feces (100 mg) from all animals were pooled on day 4 of the study and then ground into a fine paste. All samples were sonicated and sequentially refluxed in 80% methanol for 2 hours and chloroform/methanol (1:1) for 1 hour. Samples were taken to dryness, and the dried extracts were resuspended in 80% methanol (20 mL). Fractions of the methanolic extract (1/40 of intestinal contents and 1/20 of feces samples) were removed and the internal standard nordeoxycholic acid (10 μg) was added. This extract was diluted with 0.01 mol/L acetic acid (20 mL) and passed first through a column of Lipidex 1000 (bed size, 4×1 cm; Packard Instrument Co., Groningen, The Netherlands) and then through a Bond-Elut $C_{18}$ cartridge (Analytichem, Harbor City, Calif.). Bile acids were recovered by elution of the Lipidex 1000 column and the Bond-Elut cartridge with methanol (20 mL and 5 mL, respectively), and the combined extracts were taken to dryness. Unconjugated bile acids were isolated and separated from neutral sterol and conjugated bile acids by lipophilic anion exchange chromatography on diethylaminohydroxypropyl Sephadex LH-20 (Lipidex-DEAP; Package Instrument Co.). Recovery of unconjugated bile acids was achieved by elution with 0.1 mol/L acetic acid in 72% ethanol (7 mL) followed by evaporation of the solvents. Total conjugated bile acids were recovered with 9 mL of 0.3 mol/L acetic acid in 72% ethanol, pH 9.6. Salts were removed by passage through a Bond-Elut $C_{18}$ cartridge after addition of nordeoxycholic acid (10 μg), and conjugated bile acids were recovered by elution with 5 mL of methanol. Solvolysis was performed in a mixture of methanol (1 mL), distilled tetrahydrofuran (9 ml), and 1 mol/L trifluoracetic acid in dioxane (0.1 mL) and heated to 45° C. for 2 hours. After solvolysis, unconjugated bile acids were isolated by chromatography on Lipidex-DEAP. Methyl ester derivatives were prepared by dissolving the sample in methanol (0.3 mL) and reacting with 2.7 mL of freshly distilled ethereal diazomethane. After evaporation of the reagents, the methyl ester derivatives were converted to trimethylsilyl ethers by the addition of 50 mL of Tri-Sil reagent (Pierce Chemicals, Rockford, Ill.). A column of Lipidex 5000 (Packard Instrument Co.) was used to remove derivatizing reagents and to purify the sample.

Unconjugated and Sulfate Bile Acids In Plasma And Urine

In each group, urine from all animals was pooled on the individual days of collection. Day 1 represented the baseline sample, and samples from days 2, 3 and 4 were obtained during bile acid administration. After the addition of nordeoxycholic acid (1 $\mu$g), bile acids were quantitatively extracted from portions of urine (3 mL) and plasma (1 mL) using Bond-Elut $C_{18}$ cartridges. After liquid-solid extraction, isolation and separation of unconjugated and conjugated bile acids were achieved by lipophilic anion-exchange chromatography on Lipidex-DEAP. Solvolysis of bile acid conjugates and isolation of the hydrolyzed products were performed as described above, and bile acids were converted to volatile methyl ester-trimethylsilyl ether derivatives.

Extent of Bile Acid Conjugation in Liver and Jejunal Contents

Samples of liver (100 mg) were ground to a fine paste, and bile acids were extracted by reflux and passage through a column of Lipidex 1000 as described above for intestinal contents and feces. Group separation of bile acids, according to their mode of conjugation was achieved by lipophilic anion-exchange chromatography. Extracts from each animal were pooled, and bile acids and their conjugates were separated using Lipidex-DEAP and stepwise elution of the gel bed with the following buffers: 0.1 mol/L acetic acid in 72% ethanol (unconjugated bile acids): 0.3 mol/L acetic acid in 72% ethanol, pH 5.0 (glycine conjugates); 0.15 mol/L acetic acid in 72% ethanol, pH 6.5 (taurine conjugates); and 0.3 mol/L acetic acid in 72% ethanol, pH 9.6 (sulfate conjugates). After evaporation of the buffers, sulfated bile acids were solvolyzed, whereas amidated conjugates were hydrolyzed with 50 U of cholylglycine hydrolase (Sigma Chemical Co.) in 2.5 mL of 0.2 mol/L phosphate buffer, pH 5.6, at 37° C. overnight. The resulting unconjugated bile acids were isolated on Upidex-DEAP, and the methyl ester-trimethylsilyl ether derivatives were prepared as described above.

After solvolysis, the amidated bile acids from the jejunal portion of the rat intestine were isolated on Lipidex-DEAP by elution with 0.15 mol/L acetic acid in 72% ethanol, pH 6.5 (6 mL). Enzymic hydrolysis was performed as described above, and the resulting unconjugated bile acids were isolated and derivatized as described above.

GC-MS

The methyl ester-trimethylsilyl ether derivatives were separated on a 30 m×0.25 mm DB-1 fused silica capillary column (J&W Scientific, Folson, Calif.) using a temperature program from 225° C. to 295° C. with increments of 2° C./min and a final isothermal period of 30 minutes. GC-MS analysis was performed using a Finnigan 4635 mass spectrometer (Finnigan Inc., San Jose, Calif.) that housed an identical gas chromatography column operated under the same conditions. Electron ionization (70 eV) mass spectra were recorded over the mass range of 50–800 daltons by repetitive scanning of the eluting components. Identification of bile acids was made on the basis of the gas chromatography retention index relative to a homologous series of n-alkanes, referred to as the methylene unit value, and the mass spectrum compared with authentic standards. Quantification of bile acids was achieved using gas chromatography by comparing the peak height response of the individual bile acids with the peak height response obtained from the internal standard.

Liquid Secondary Ionization Mass Spectrometry

Liquid secondary ionization mass spectrometry negative ion spectra of urine samples were obtained after placing approximately 1 $\mu$L of the methanolic extract onto a small drop of a glycerolimethanol matrix spotted on a stainless steel probe. this probe was introduced into the ion source of a VG Autospec Q mass spectrometer, and a beam of fast atoms of cesium, generated from cesium iodine (35 KeV), was fired at the target containing the sample. Negative ion spectra were obtained over the mass range of 50–1000 daltons.

STATISTICAL ANALYSIS

Data are expressed as mean±SEM or as mean values of all animals when extracts were pooled before analysis. Results from different groups were compared using paired and unpaired two-tailed Student's t-test. P values of <0.05 were considered statistically significant.

RESULTS

Intraluminal Bile Acid Composition Along The Intestine

The average weight of the resected segments of intestine for the animals in the control group and those administered the individual bile acids were similar. In control animals, the total amount of UDCA in the jejunum (0.03±0.01 mg) was negligible, accounting for only 0.3% of the total bile acids. However, the total mass of UDCA (and its percentage of the total bile acids) in the jejunum was greater in all animals 24 hours after the administration of the final dose of UDCA, UDCA 3-sulfate, UDCA 7-sulfate and UDCA 3,7-disulfate, accounting for 9.95±0.49 mg (35.9%), 3.67±0.45 mg (16.4%), 1.09±0.34 mg (4.7% and 0.21±0.07 mg (2.0%), respectively. This result indicates very little conservation of UDCA when a sulfate group is conjugated in the C-7 position (Table 1).

$\Delta^{22}$ UDCA, a specific metabolite of exogenously administered UDCA, was detected in large proportions and amounts of the jejunum of animals administered UDCA and UDCA 3-sulfate. However, this metabolite was not detected in the control group and accounted for <3% of the total jejunal bile acids of the animals administered the C-7 sulfate conjugates of UDCA (Table 1).

When the conjugation pattern for UDCA in the jejunum was examined after separation of the bile acids by lipophilic anion-exchange chromatography (FIG. 1), animals administered UDCA were found to have predominantly glyco- and tauro-UDCA, smaller amounts of unconjugated UDCA, and negligible amounts of sulfated UDCA. Although amidated and unconjugated forms of UDCA were found in the jejunum after administration of the C-7 sulfates, the total mass of UDCA in the jejunum was very small. In rats administered UDCA-3-sulfate, the jejunum contained substantial proportions of amidated UDCA, indicating significant biotransformation by deconjugation and/or amidated.

With regard to endogenous bile acids, cholic acid was the major bile acid in the jejunum of the control animals, accounting for 48.5%±2.9% (6.82±1010 mg) of the total bile acids, and after UDCA administration, there was a significant decrease (P=0.01) to 16.8%±1.3% (4.68±0.65 mg). UDCA 3-sulfate also caused a decrease (P=0.05) in the proportion of cholic acid but to a lesser extent than UDCA, whereas administration of the C-7 sulfates of UDCA caused an increase (P=0.01) in the proportion of cholic acid in the jejunum (Table 1).

In the colon of the control animals, most of the bile acids were secondary and were identified mainly as deoxycholic and ω-muricholic acids, but only small amounts of lithocholic acid were detected (Table 2). UDCA administration caused a decrease (P=0.003) in the proportion of deoxycholic acid, and lithocholic acid became the major bile acid present, accounting for 32.0%±0.8% of the total colonic bile acids (P=0.0004). In contrast, UDCA 7-sulfate and UDCA 3,7-disulfate administration led to substantial reductions in the mass and proportion of both deoxycholic acid and lithocholic acid in the colon.

FECAL BILE ACID EXCRETION

Figure 3:
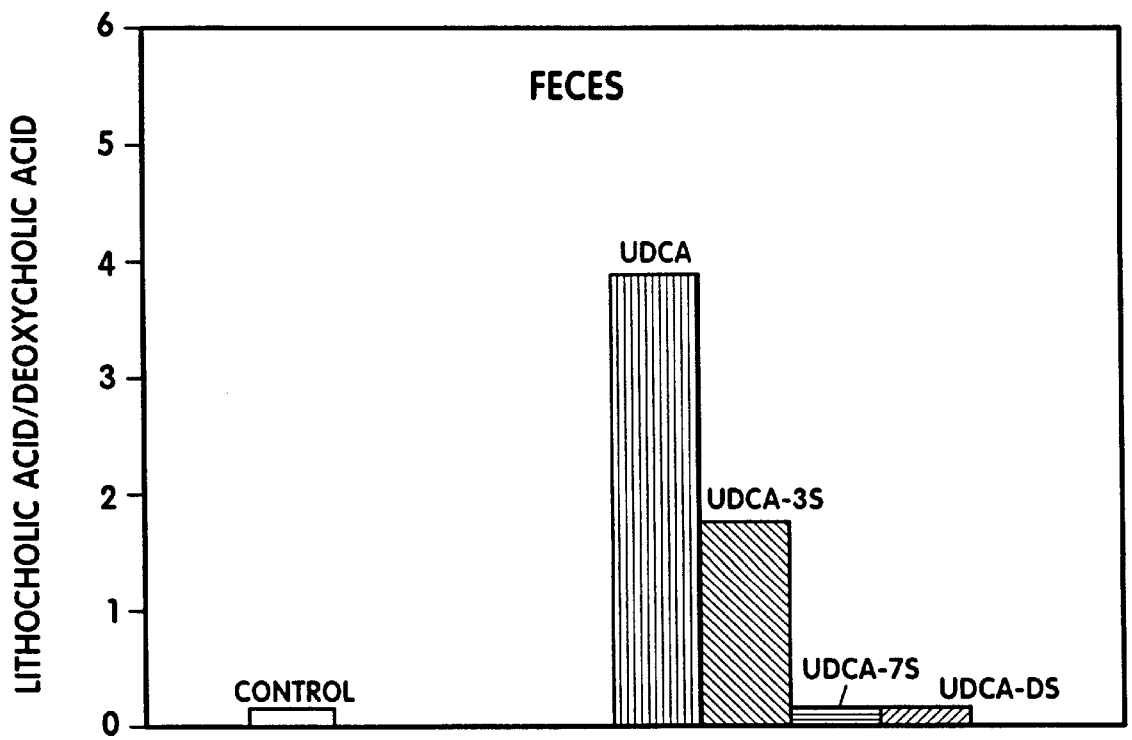
FIG. 3 shows the ratio of lithocholic acid/deoxycholic acid in the feces of control rats and rats orally administered UDCA, UDCA 3-S, UDCA 7-S and UDCA-DS. Results are expressed as the mean values of all animals.
Figure 4A:
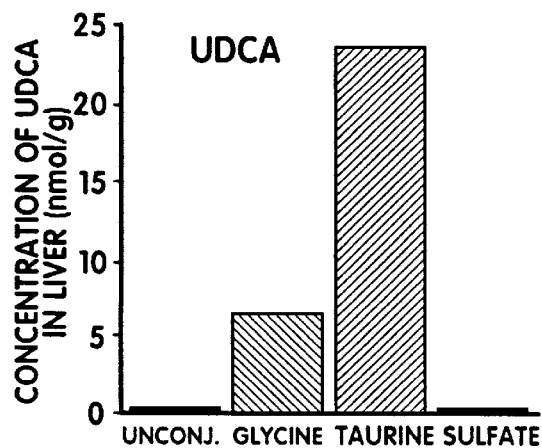
FIGS. 4A–4D show UDCA concentration in liver tissue of rats orally administered UDCA (FIG. 4A), UDCA 3-S (FIG. 4B), UDCA 7-S (FIG. 4C) and UDCA-DS (FIG. 4D). Bile acids were separated according to their mode of conjugation by anion-exchange chromatography before analysis of the individual fractions using GC-MS. Results are expressed as mean values of all animals.
Figure 4B:
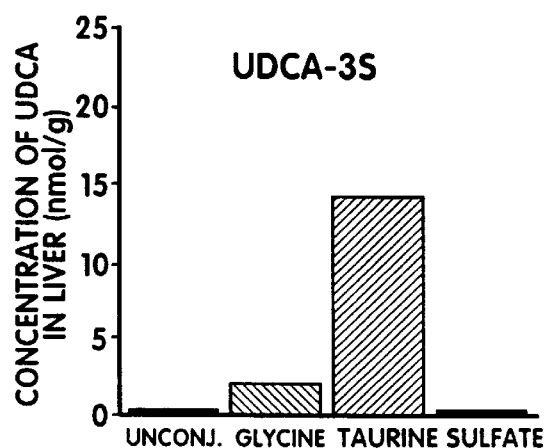
Figure 4C:
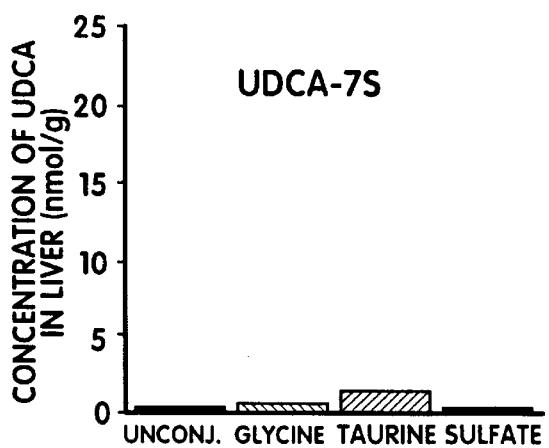
Figure 4D:
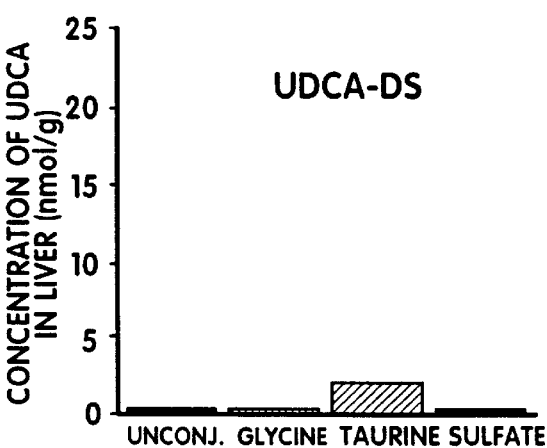

No significant differences were found in the weight of feces excreted each day among the groups of animals. Total fecal bile acid excretion in animals administered UDCA, UDCA 3-sulfate, UDCA 7-sulfate, and UDCA disulfate was 14.85, 10.70, 12.65 and 10.88 mg/g feces, respectively. The feces of all animals became enriched with UDCA; however, for those animals administered the unconjugated bile acid, UDCA was almost exclusively found in the unconjugated form. In contrast, there were negligible concentrations of unconjugated UDCA in the feces of rats administered UDCA 7-sulfate and UDCA 3,7-disulfate; these two conjugates were excreted in feces virtually unchanged (FIG. 2). The concentrations of the major secondary bile acids excreted in feces differed among the groups of animals. In the UDCA group, lithocholic acid increased markedly from control values, whereas the fecal excretion of lithocholic acid after UDCA 7-sulfate and UDCA 3,7-disulfate administration was reduced. A similar trend in deoxycholic acid excretion was found. Compared with normal rat feces, the ratio of lithocholic acid/deoxycholic acid increased more than 20-fold when UDCA was administered, increased 11-fold with UDCA 3-sulfate administration, and did not increase when the C-7 sulfates were administered (FIG. 3).

Bile Acid Composition of Liver Tissue

The concentration and proportions of the individual bile acids in liver tissue are summarized in Table 3. UDCA concentration was 12.0 nmol/g in control animals, and accounted for 2.8% of the total hepatic bile acids. Administration of UDCA and the C-3 sulfate caused increased concentrations and proportions of liver tissue UDCA (FIG. 1). In addition, $\Delta^{22}$ UDCA was found in the liver in relatively high proportions. In contrast, marked decreases in the total UDCA concentration and percent composition occurred when animals were administered the C-7 sulfate bile acids. UDCA administration resulted in increased hepatic lithocholic acid concentration, whereas decreases in lithocholic acid occurred after administration of the sulfate conjugates. Deoxycholic acid concentration decreased in all groups with bile acid administration, and the reduction was greater for the C-7 sulfates. Liver tissue cholic acid concentration decreased almost 4-fold when UDCA was administered but increased slightly after administration of the C-7 sulfate conjugates.

After administration of the individual bile acids, the conjugation of UDCA in liver tissue established that unconjugated UDCA and its C-3 sulfate were both biotransformed by conjugation, mainly with taurine. Irrespective of the administered bile acid, negligible concentrations and proportions of unconjugated UDCA and sulfated UDCA were found in the liver tissue of all animals (FIG. 4).

Bile Acid Composition of Plasma and Urine

Unconjugated plasma UDCA concentration in animals administered UDCA was 4.8±2.2 μmol/L, and this value was significantly greater than that found for animals administered UDCA 3-sulfate (0.9±0.4 μmol/L), UDCA 7-sulfate (0.7±0.5 μmol/L) and UDCA disulfate (1.0±0.2 μmol/L. Sulfated UDCA concentrations were similar and <0.3 μmol/L in all animal groups.

The urinary excretion of UDCA was negligible (<0.4 nmol/day) before bile acid administration for all animals. After UDCA, urinary unconjugated UDCA excretion was 642.7 nmol/day. This was significantly greater than the concentration of UDCA excreted in the urine of the animals administered the sulfate conjugates (UDCA 3-sulfate, 5.2 nmol/day; UDCA 7-sulfate, 1.8 nmol/day; and UDCA 3,7-disulfate, 1.3 nmol/day). Sulfate conjugates of UDCA were also found in the urine after the administration of unconjugated UDCA (4.6 nmol/day), UDCA 3-sulfate (2.7 nmol/day), UDCA 7-sulfate (317.8 nmol/day), and UDCA 3,7-disulfate (217.1 nmol/day). Although this represents <0.05% of the daily dose. administered, it was possible to detect these bile acid conjugates by liquid secondary ionization mass spectrometry analysis.

DISCUSSION

Liver tissue UDCA concentrations increased markedly with oral administration of UDCA, and this bile acid was predominantly conjugated by amidation. Negligible amounts of unconjugated UDCA were found (FIG. 4), and in this regard, its metabolism is similar to that of humans. In contrast, when the C-7 sulfate and the disulfate conjugates were administered, hepatic concentrations of UDCA were low compared with the control animals, indicating that these conjugates were not absorbed from the intestine and thus, there was negligible conservation of UDCA. Hepatic UDCA concentrations increased after administration of the C-3 sulfate, and the fact that it was mainly amidated indicated that significant desulfation and amidation of UDCA 3-sulfate had taken place. The pattern of conjugation of UDCA in the jejunum paralleled that of the liver tissue except that, in the UDCA and UDCA 3-sulfate administered groups there was a higher proportion of unconjugated UDCA present (FIG. 1). Previous studies of bile acid feeding had established that maximum enrichment of the bile acid pool is attained by 4 days and prolonged feeding results in no further changes in bile acid composition.

The lack of intestinal absorption of the C-7 sulfates of UDCA is further reflected in the bile acid composition of feces. The fecal concentration of the total amount of UDCA in the animals administered UDCA 7-sulfate and UDCA 3,7-disulfate was markedly greater than that found in the feces of animals administered UDCA or UDCA 3-sulfate. In addition, the C-7 sulfates of UDCA were predominantly excreted unchanged in feces. These findings can be explained by the substrate specificity of bacterial sulfates, which have been previously shown to be active only toward C-3 bile acid sulfates. UDCA administration had a marked effect on the fecal excretion of the major secondary bile acids and lithocholic and deoxycholic acids. A large increase in the fecal lithocholic acid concentration occurred when unconjugated UDCA and UDCA 3-sulfate were administered, but UDCA 7-sulfate and UDCA 3,7-disulfate administration had no significant effect on the fecal output of these secondary bile acids.

The increases in fecal and hepatic lithocholic acid concentrations can be explained by intestinal bacterial biotransformation of UDCA and, to a lesser extent, its C-3 sulfate. Biotransformation of UDCA to lithocholic acid occurs to a similar extent in both rats and humans. An increase in deoxycholic acid in the feces of animals administered UDCA is consistent with the known competitive inhibition of cholic acid uptake at the terminal ileum, which leads to an increased spill-over into the colon and subsequent 7α-dehydroxylation to form deoxycholic acid. Interestingly, the UDCA C-7 sulfates seem to have the opposite effect; cholic acid concentrations in liver tissue were increased slightly compared with control animals, and fecal cholic acid and deoxycholic acid concentrations were decreased.

In view of the fact that UDCA undergoes significant biotransformation to lithocholic acid and increases fecal deoxycholic acid concentration, both highly hydrophobic bile acids, it is perhaps surprising that beneficial effects of UDCA have been shown in animal models of chemically induced colon cancer. In these models, it has been established conclusively that hydrophobic bile acids promote tumor growth. Rectal and oral administration of bile acids, bile diversion to the cecum, cholestyramine feeding, dietary fat, and certain fibers, conditions that all increase the flux of bile acids through the colon, enhance tumor formation, consistent with a promoting effect. In vitro studies indicate that deoxycholic and lithocholic acids are comitogenic and increase the colonic epithelial cell proliferation rate. Other effects on ornithine decarboxylase activity and HLA class I and II antigens have also been shown.

There are several possible explanations for the chemopreventive effect of UDCA. Any deleterious effects of increased lithocholic acid formation in the colon may be buffered by the presence of relatively high concentrations of UDCA in a manner similar to the cytoprotective effects of UDCA when coincubated in vitro or coninfused in vivo with hydrophobic bile acids that are membrane damaging. Alternatively, the protective effects may be the result of decreased colonic deoxycholic acid concentration, which would imply that deoxycholic acid is of major importance in the promotion of colon cancer. Despite similar reductions in colonic deoxycholic acid with administration of the sulfated bile acids, the C-7 sulfates of UDCA may in principle be superior to UDCA because these conjugates are not biotransformed to more hydrophobic bile acids. Additionally, the lack of absorption of the C-7 sulfates in the small intestine may permit the use of lower doses to attain similar chemopreventive effects.

The role of bile acids in human colonic carcinogenesis is less clear. Early studies indicate that fecal bile acid excretion, particularly lithocholic and deoxycholic acids, was increased in patients with colon cancer, adenomatous polyps, and familial polyposis, although these findings were not substantiated by several other investigators. Compared with controls, patients with colonic cancer or adenomatous polyps have been reported to have increased aqueous-phase lithocholic and deoxycholic acids concentrations in feces, and these concentrations correlated with the extent of colonic cell proliferation. Despite preliminary data supporting a chemoprotective and/or cytoprotective effect of UDCA in animal models of colon cancer and in vitro cell systems, the increased lithocholic acid formation after UDCA administration may limit the overall effectiveness of UDCA in the colon. The lithocholate/deoxycholate ratio in feces is markedly increased after UDCA and UDCA 3-sulfate administration compared with controls (FIG. 3). This may be less desirable because the ratio of fecal lithocholate/deoxycholate is increased in patients with colon cancer and in patients at high risk for the disease and is proposed to be of diagnostic value. On the other hand, UDCA 7-sulfate and UDCA 3,7-disulfate administration resulted in no change in the lithocholate/deoxycholate ratio. Although not statistically significant, a tendency towards a decrease in this ratio was observed, whereas the quantitative fecal excretion of these secondary bile acids was similar to control animals.

Furthermore, as discussed above, the introduction of a sulfate group at the position C-7 of UDCA greatly increases the hydrophilicity of the molecule, which prevents intestinal absorption, thereby facilitating the site-specific delivery of UDCA to the colon. In contrast to unconjugated UDCA, which undergoes conversion to lithocholic acid, thereby increasing the fecal lithocholic/deoxycholic acid ratio, considered a risk factor for colonic disease, the C-7 sulfates are metabolically inert. Therefore, these conjugated bile acids may be more effective chemoprotective agents than UDCA in the colon.

METABOLISM AND EFFECT OF SULFATE ESTERS OF USODEOXYCHOILIC ACID ON BILE-FLOW AND BILIARY LIPID SECRETION IN RATS

The C-3 and C-7 sulfate esters and the disulfate conjugate of UDCA were prepared as discussed in step-by-step detail immediately below. Subsequently, the hepatic metabolism of these bile acids in the bile fistula was examined, and these bile acids were compared with UDCA to establish their effect on bile-flow and biliary lipid secretion.

MATERIALS AND METHODS
Synthesis of Ursodeoxycholic Acid 3-sulfate (UDCA-3S)

Imidazole (3.5 g) and tert-butyldimethylsilyl chloride (1.6 g) was added to an ice-cold solution of UDCA (2 g) in anhydrous dimethylformamide (1.5 ml)-pyridine (0.75 ml) and the mixture was stirred for 30 min. The reaction mixture was then poured into ice water (20 ml) and extracted with ethyl acetate (100 ml). The organic layer was washed with water, dried over anhydrous $Na_2SO_4$, and evaporated. The oily residue obtained was dissolved in hexane-ethyl acetate (3:1 by vol, 250 ml) and filtered through a 40 g of column of silica gel (28–200 Mesh, Aldrich Chemical Co. Inc., Wisconsin). After evaporation of the solution the residue was dissolved in ethanol and the product, UDCA-3-tbDMS ether (2.15 g, yield 83%) was crystallized. Treatment of UDCA-3tBDMS ether (2.0 g) with acetic anhydride (20 ml) and pyridine (20 ml) at room temperature for 5 yielded UDCA 7-acetate 3-tbDMS ether as an oily product. To a solution of UDCA 7-acetate 3-tbDMS ether in acetone (24 ml) was added 18% HCl (2.4 ml) and the mixture was stirred at room temperature for 30 min. The resultant product was extracted into ethyl acetate, washed with water, dried over anhydrous $Na_2SO_4$, and the solvent evaporated to give ursodeoxycholic acid 7-acetate as an oily product. Chlorosulfonic acid (1.2 ml) in anhydrous pyridine (12 ml) was added to an ice cold solution of UDCA 7-acetate (1.2 g) and the solution was heated to 50° C. After 30 minutes, the reaction mixture was terminated by addition of water (400 ml) and the product was absorbed onto a large cartridge of octadecylsilane bonded silica, MEGA-BOND-ELUT (Varian, Harbor City, Calif.) and recovered by elution with methanol. The methanolic extract was then evaporated to dryness and the pyridinum sale of UDCA 7-acetate 3-sulfate was then converted to the di-sodium salt by dissolving in 0.2M methanolic NAOH solution (40 ml) and filtered. The filtrate was diluted with cold ether (400 ml), and the precipitate was collected, washed with cold ether and dried. The solid (1.0 g) was dissolved in MeOH (10 ml), 3.5M NAOH (10 ml) was added and the solution was stirred at room temperature for 18 h. The product was extracted by MEGA-BOND-ELUT after diluting with water (500 ml). The methanolic extract from the cartridge was evaporated to dryness, dissolved in 0.2M methanolic NAOH (30 ml) and filtered. The filtrate was diluted with cold ether (300 ml), and the resulting precipitate was collected and washed with ether. The procedure was repeated three times with methanol (20 ml) and ether (200 ml) to yield the di-sodium salt of UDCA-3-sulfate (0.62 g, yield 50%).

Synthesis of Ursodeoxycholic Acid 7-sulfate (UDCA-7S)

Chlorosulfonic acid (0.9 ml) in anhydrous pyridine (9 ml) was added to an ice cold solution of UDCA 3-tbDMS ether (900 mg) and mixture was heated to 50° C. After 30 minutes, the reaction was terminated by addition of water (400 ml). The precipitate pyridinum salt of UDCA 3-tbDMS 7-sulfate was washed with water, dried under vacuum and hydrolyzed with HCl as described above. The product was extracted with a cartridge of MEGA-BOND-ELUT and the methanolic extract was evaporated to dryness and dissolved in 0.2M methanolic NaOH (30 ml.). The methanolic solution was diluted with cold ether (300 ml), and the precipitated di-sodium salt was then isolated as described above to obtain the pure di-sodium salt of UDCA-7-sulfate (640 mg, yield 76%).

Synthesis of Ursodeoxvcholic Acid 3,7-disulfate (UDCA-DS)

Chlorosulfonic acid (1 ml) in pyridine (10 ml) was added to an ice cold solution of UDCA (1 g) in anhydrous pyridine (10 ml) and the mixture was heated to 50° C. After 60 minutes, the reaction with terminated by addition of water (500 ml). The product was extracted with a cartridge of MEGA-BOND-ELUT and isolated as described above to yield the di-sodium salt of UDCA-disulfate (1.1 g, 91% yield).

Gas chromatography-mass spectrometry (GC-MS) was used to confirm the position of the sulfate groups in all synthesized compounds after oxidation, solvolysis and conversion to methyl trimethylsilyl (Me-TMS) ether derivatives. Chromatographic purity of the synthetic compounds was found to be >97% as determined by high-pressure liquid chromatography (HPLC), thin-layer-chromatography (TLC) and capillary column gas chromatography (GC).

Animal Studies

Adult male Sprague-Dawley rats (body weight 200–230 g) were anesthetized by an intraperitoneal injection of pentobarbital (Nembutal, 7.5 mg/100 g body weight), and maintained under sedation by additional doses. The right jugular vein and the common bile duct were cannulated using PE-50 polyethylene tubing (Clay-Adams, Parsippany, N.J.). Body temperature was maintained throughout the experiment at 37° C. using a rectal probe and a thermostatically controlled heating pad (Harvard Apparatus Co., Inc., Millis, Mass.). Saline was infused at a rate of 1.0 ml/h using a Harvard pump (Harvard Apparatus Co., Inc.) into the jugular vein for a control period of 2 h. After collecting two 10 minute bile samples for base-line analysis, the bile acids were individually infused intravenously (i.v.) for 30 minutes in stepwise increasing doses (0.5, 1.0, and 2.0 $\mu$mol/min/100 g body weight). Bile acid solutions were prepared in 3% human albumin in 0.45% saline. Six animals were used for each experiment and bile was collected every 10 minutes into preweighed tubes. At the end of the experiment, blood was obtained by cardiac puncture, and urine was obtained by aspiration of the bladder. All biological specimens were stored at −20° C. This animal study protocol (#1B10044) was approved by the Bioethics committee of the Children's Hospital Medical Center (Cincinnati, Ohio).

Analytical Techniques

TLC was performed on precoated silica gel G plates (Merck, 0.2 mm thickness) using a solvent system of n-butanol-acetic acid-water (10:1:1, by vol). The spots were visualized by spraying with a 10% ethanolic solution of phosphomolybdic acid followed by heating at 120° C. for 5 minutes.

HPLC was performed using a Varian 5000 HPLC instrument (Varian Associates Inc., Palo Alto, Calif.) equipped with a variable wavelength UV detector and housing a 25×0.46 cm Hypersil ODS column (5 $\mu$m particle size; Keystone Scientific, Bellefonte, Pa.). The column was operated at ambient temperature and the eluting solvent was methanol –0.01 M phosphate buffer (65:35, by vol), adjusted to pH 6.8 and modified from the method of Rossi et al. (High pressure liquid chromatographic analysis of conjugated bile acids in human bile: simultaneous resolution of sulfated and unsulfated lithocholyl amidates and the common conjugated bile ducts. *J. Lipid Res*. 28: 589–595 (1987)). Flow rate was 1.0 ml/min and bile acids were detected by absorption at 205 nm.

GC was carried out on a Hewlett-Packard 5890 gas chromatograph housing a 30 meter DB-1 (4 mm i.d.; 0.25 $\mu$m film) fused silica capillary column (J and W Scientific Inc., Rancho Cordova, Calif.) and using a temperature program from 225° C. to 295° C. in increments of 2° C./min with initial and final isothermal periods of 2 minute and 30 minutes respectively. Helium was used as the carrier gas with a flow-rate of 1.8 milmin.

GC-MS was carried out on either a VG Autospec Q magnetic sector instrument or a Finnigan 4635 quadruple GC-MS-DS instrument housing identical GC columns and operated under the same chromatographic conditions. Electron ionization (70 eV) mass spectra were recorded over the mass range 50 to 1000 Dale by repetitive scanning of the eluting components.

Negative ion fast atom bombardment-mass spectrometry (FAB-MS) spectra of bile samples, urine and synthetic compounds were obtained after placing the equivalent of approximately 1 $\mu$l of the original bile extract, 10 $\mu$l–50 $\mu$l of the urine extract and $\mu$g quantities of synthetic bile acids dissolved in methanol onto a small drop of a glycerol matrix spotted on a copper target of the FAB probe. This probe was introduced directly into the ion source of the mass spectrometer and a beam of fast atoms of either xenon generated with a saddle field atom gun (ion Tech, Teddington, Middlesex, UK) operated at 8 kV and 20 $\mu$A, or cesium generated from cesium iodine (35 kV), was fired at the target containing the sample. Negative ion spectra were obtained over the mass range of 50–1000 Da/e.

Bile Analysis

Bile volume was determined gravimetrically assuming a density of 1 g/ml. Total 3$\alpha$-hydroxy bile acid concentration in the bile was measured enzymatically before solvolysis (nonsulfated bile acids) and after solvolysis (total bile acids) (Mashige, F., et al., Direct spectrometry of total bile acids in serum. *Clin. Chem*. 27: 1352–1356 (1981)). The bile acid output was calculated by multiplying the rate of bile-flow by the bile acid concentration. Biliary phospholipids were determined by an enzymatic procedure based on the choline oxidase method (Nippon Shoji Kaisha, Ltd., Osaka, Japan) (Grantz, D., et al., Enzymatic measurement of choline-containing phospholipids in bile. *J. Lipid Res*. 22: 273–276 (1981)). Cholesterol was also measured enzymatically (Boehringer Mannehim, Indianapolis, Ind.) (Fromm, H., et al., Use of a simple enzymatic assay for cholesterol analysis in human bile. *J. Lipid Res.* 21: 259–261 (1980)).

Biliary and Urinary Bile Acid Analysis

For the determination of hepatic biotransformation of the infused bile acid, bile collections from the six animal were pooled and biliary bile acids were determined by GC-MS after extraction, solvolysis, hydrolysis, and derivatization. Quantification of bile acids was achieved using GC, by comparing the peak height response of the individual bile acid with the peak height response obtained from the internal standard, nordeoxycholic acid added to the initial sample of bile. Identification of a bile acid was made on the basis of the retention index relative to a homologous series of n-alkanes, referred to as the methylene unit value (MU) and the fragmentation pattern of the mass spectrum was compared with authentic standards. A list of over 100 mass spectra of authentic bile acid standards and retention indices was recently compiled as a reference source (Lawson, A. M., et al., Mass spectrometry of bile acids, *The Bile Acids*, Vol. 4, Methods and Applications, pp. 167–267 (1988)). Urine collections from the six animals were pooled and the bile acids were extracted by liquid-solid extraction using a Bond Elut-$C_{18}$ cartridge and bile acids were analyzed by GC-MS after solvolysis, hydrolysis and derivatization.

Group Separation of Bile Acids Using Lipophilic Anion Exchange Chromatography

In the case of the animals infused with UDCA-3S, bile was collected during the final period of bile acid infusion (1.0 μmol/min/100 g body weight). Bile acids were solvolyzed and separated into groups based on their mode of conjugation using the lipophilic anion exchange gel, diethylaminohydroxypropyl Sephadex LH-20; Packard Instruments, Groningen, The Netherlands). Bile acid composition was determined in each fraction by GC-MS after hydrolysis and preparation of the Me-TMS ethers.

Statistical Methods

Results were expressed as mean +standard error of mean (SEM). Bile-flow and biliary lipid output were expressed as μl/min/g liver and nmol/min/g liver, respectively. Statistical analysis was made using INSTAT program (Graphpad Software Inc., San Diego, Calif.). Parametric data among groups were analyzed using Student's t-test. The statistical comparisons between the different groups were made by one-way analysis of variance (ANOVA). When the values were found to be significant with respect to infusions of different bile salts, the comparison of any of two groups were made by Bonferroni's t-test. Linear regression analysis was performed. The choleretic activity of each bile acid was determined from the slope of regression line of the correlation between the bile acid secretion rate and bile-flow and was expressed as μl/μmol. Comparisons between slopes were made by one-way ANOVA.

RESULTS

Bile-Flow and Bile Acid Secretion

Figure 5A:
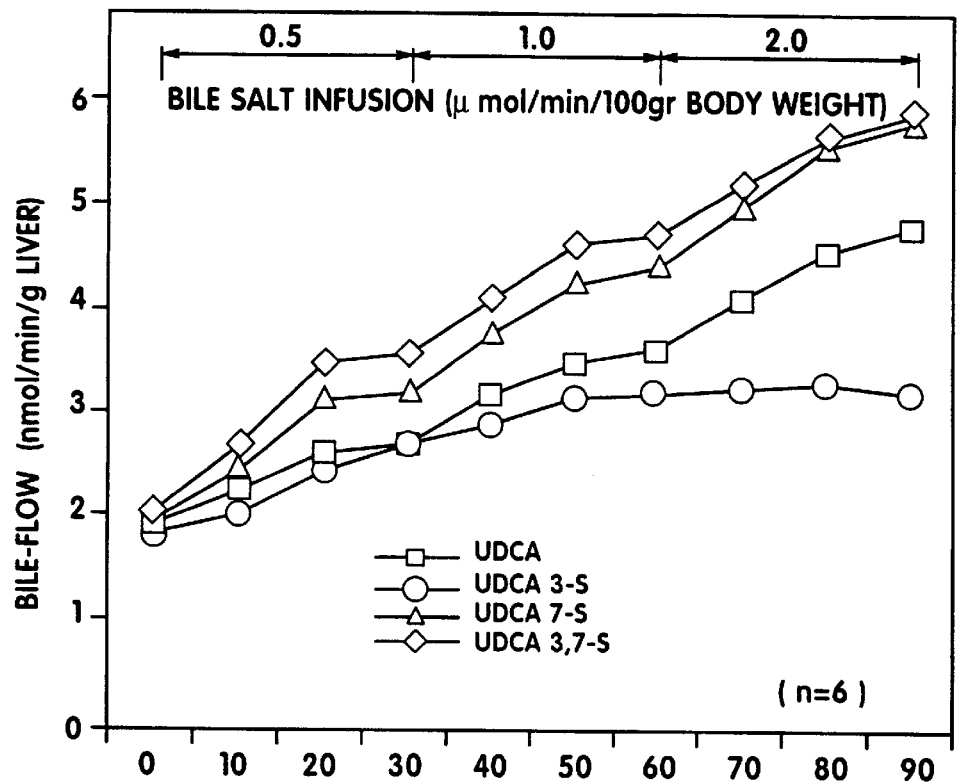
FIGS. 5A and 5B show mean biliary bile-flow and bile acid output by Sprague-Dawley rats during IV, infusion of UDCA and the sulfate conjugates.
Figure 5B:
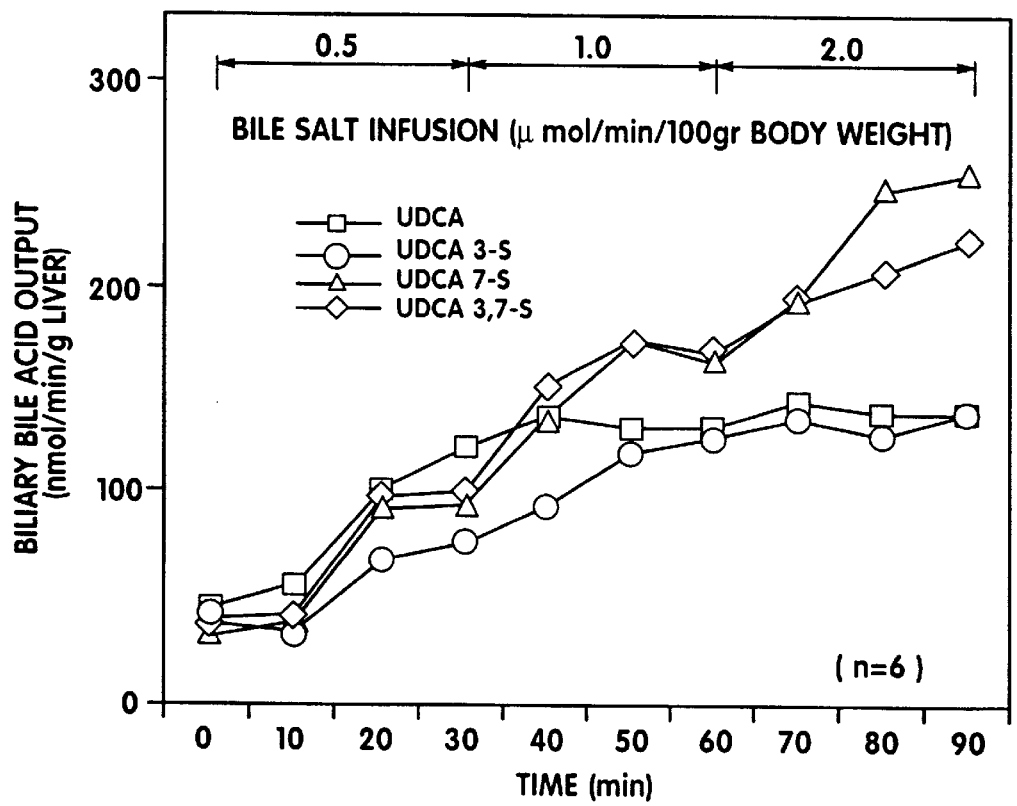
Figure 6A:
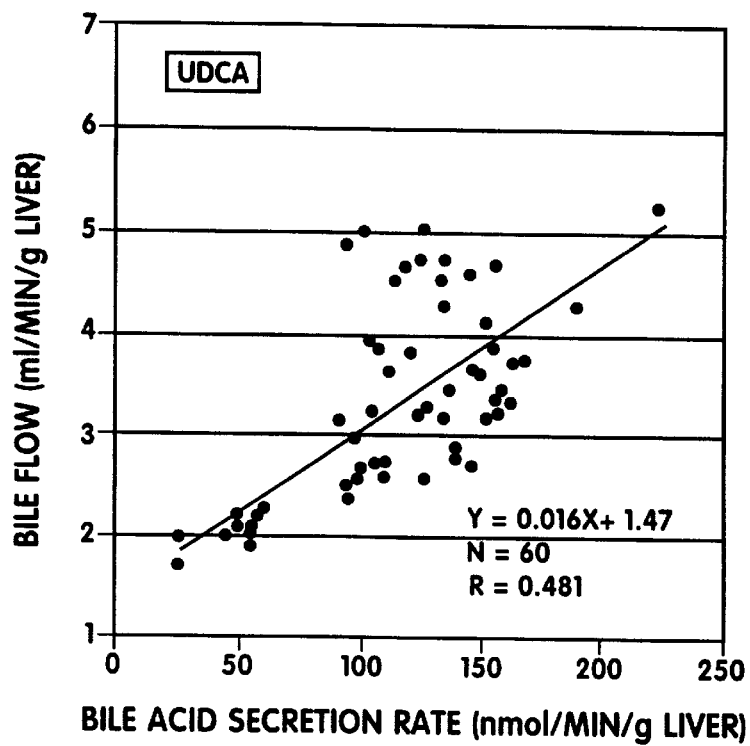
FIGS. 6A–6D show the relationship between bile acid secretion rate and bile-flow following infusion of UDCA and its sulfate conjugates.
Figure 6B:
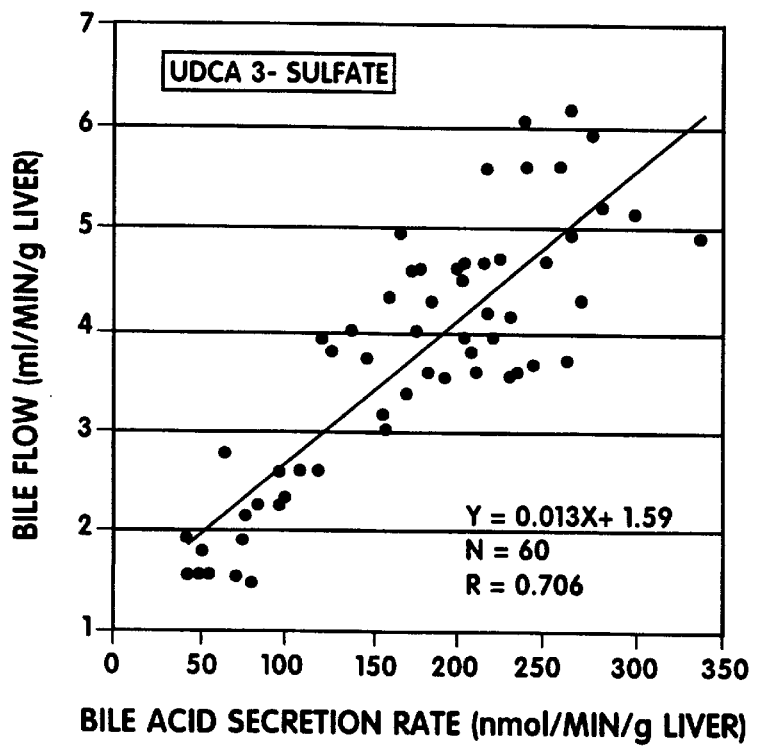
Figure 6C:
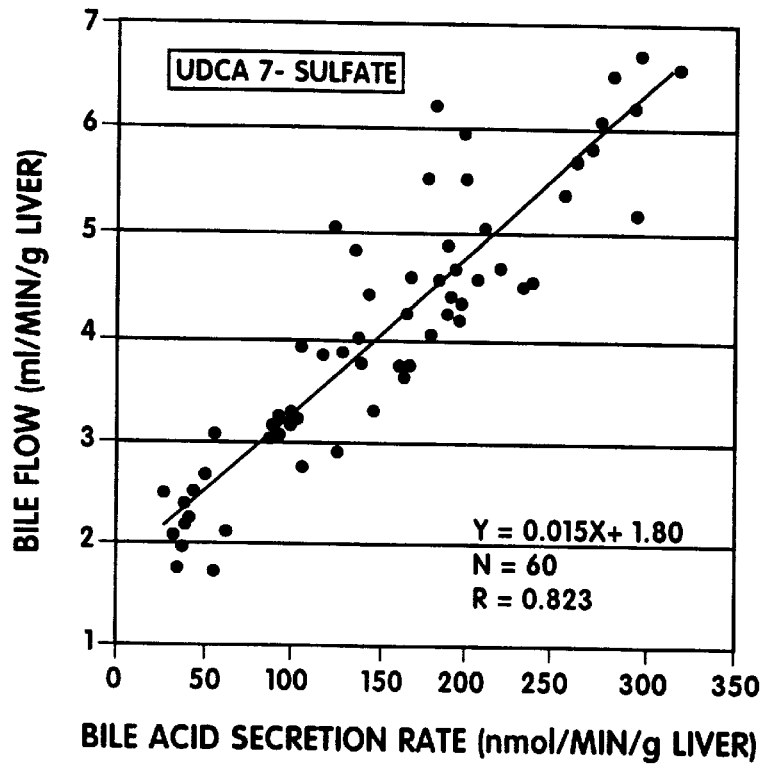
Figure 6D:
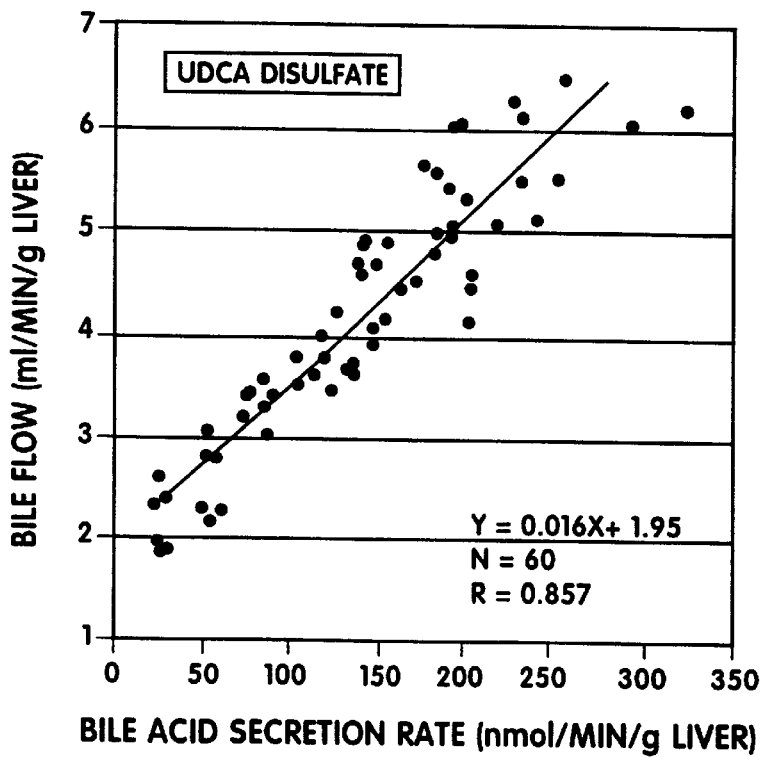

The effects of i.v. infusion of UDCA, UDCA-3S, UDCA-7S and UDCA-DS on bile-flow and bile acid secretion rate are depicted in FIGS. 5A and 5B and summarized in Table 4. All bile acids were markedly choleretic and the order of maximum bile-flow was UDCA-3S<UDCA<UDCA-7S=UDCA-DS. Biliary bile acid secretion rate increased in all animals during infusion of UDCA-3S, UDCA, UDCA-DS and UDCA-7S to a maximum of 138.9±11.8, 145.1±17.3, 222.4±24.3, and 255.4±18.2 nmol/min/g liver, respectively. For comparison, basal bile acid secretion averaged 40.4±4.2 nmol/min/g liver. The relationship between bile acid secretion rate and bile-flow following infusion of each bile acid is shown in FIG. 6. The apparent choleretic activities of UDCA, UDCA-7S, UDCA-3S and UDCA-DS calculated from the slopes of the regression lines were, 16±2, 15±1, 13±1 and 16±1 μl/μmol, respectively. The intercepts of the lines indicated bile acid-independent bile-flow was of the same magnitude (1.7 μl/min/g liver) for all the groups of animals.

Biliary Lipid Secretion

Figure 7A:
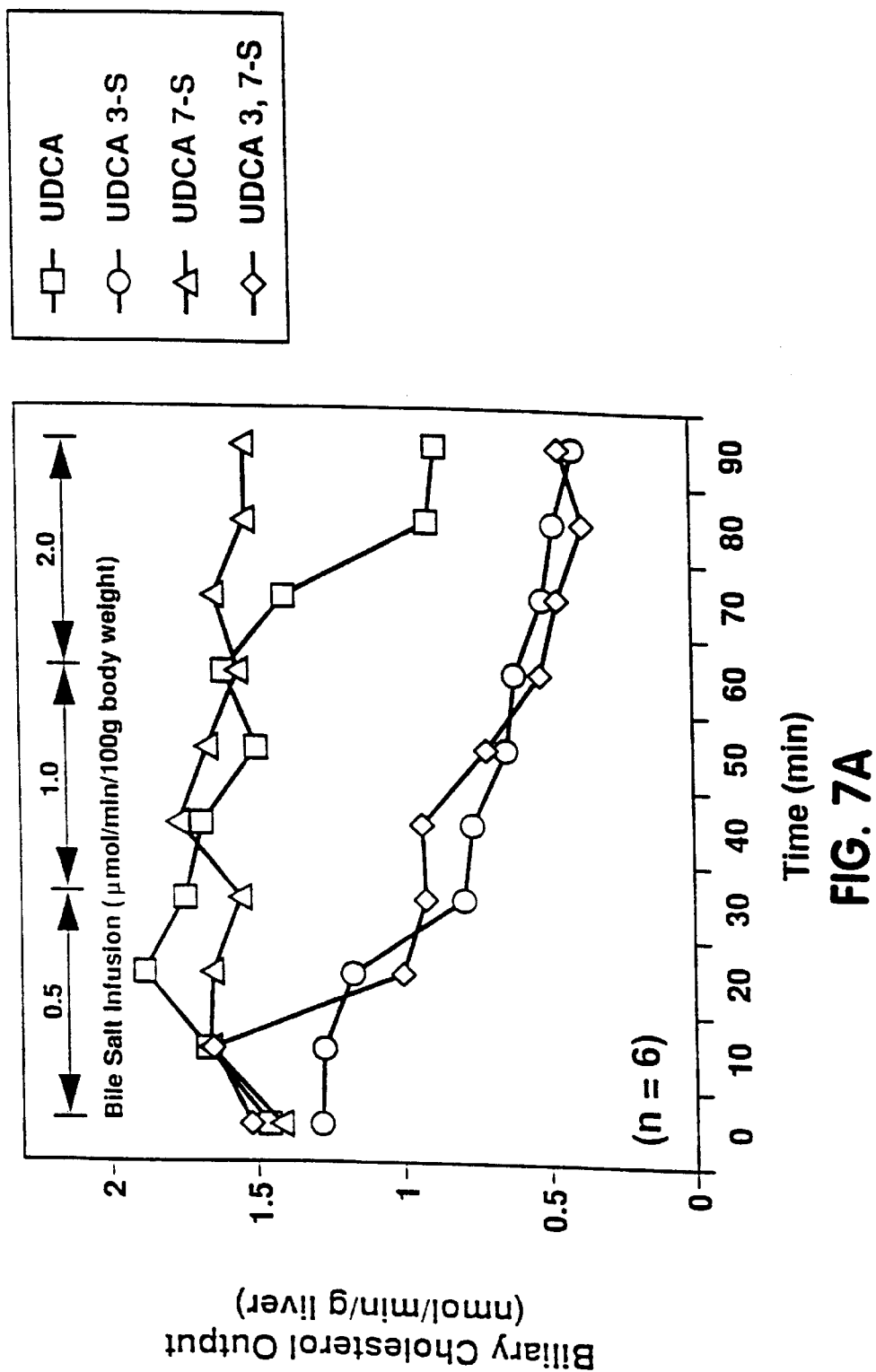
FIGS. 7A and 7B show mean biliary cholesterol and phospholipid output by Sprague-Dawley rats during IV fusion of UDCA and the sulfate conjugates.
Figure 7B:
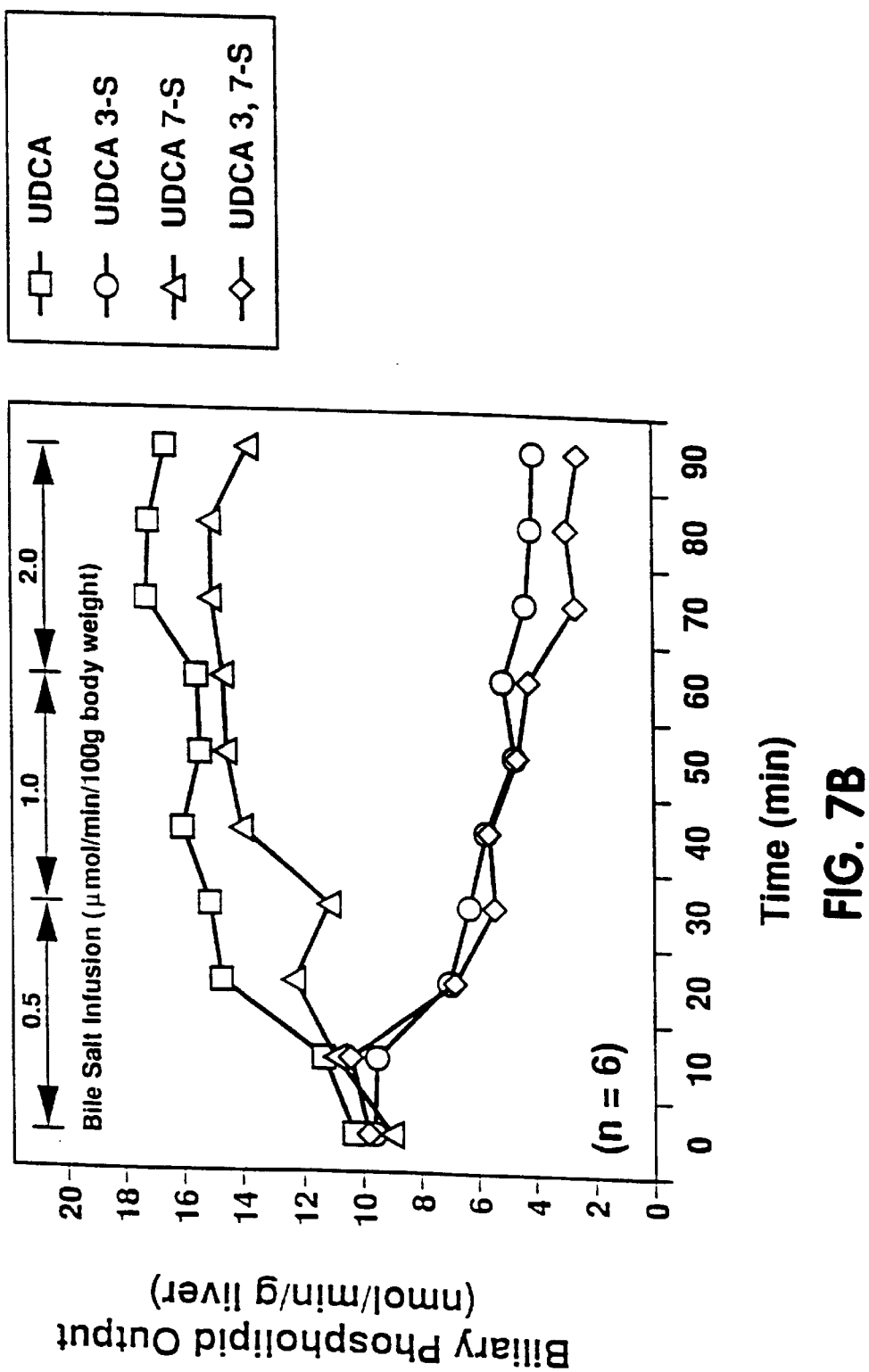

The effects of infusing UDCA and its sulfate conjugates on the biliary output of cholesterol and phospholipids are shown in FIGS. 7A and 7B. Over the first 40 minutes of infusing UDCA and UDCA-7S, biliary cholesterol increased, attaining a maximum secretion rate of 1.88±0.19 and 1.76±0.21 nmol/min/g liver respectively and cholesterol secretion was maintained with UDCA-7S but showed a significant decline when UDCA was infused even with a stepwise increase in dose. In the pre-infusion periods, the corresponding secretion rates for cholesterol averaged 1.46±0.1 and 1.42±0.16 nmol/min/g liver respectively. By contrast, infusions of UDCA-3S and UDCA-DS significantly reduced the biliary cholesterol output to 0.40±0.05 and 0.37±0.12 nmol/min/g liver respectively compared with the basal values. Biliary phospholipid secretion increased significantly with UDCA and UDCA-7S infusion, but by contrast, UDCA-3S and UDCA-DS caused a significant reduction in biliary phospholipids (Table 4).

Negative Ion FAB-MS Analysis of Biliary and Urinary Bile Acids

Figure 8A:
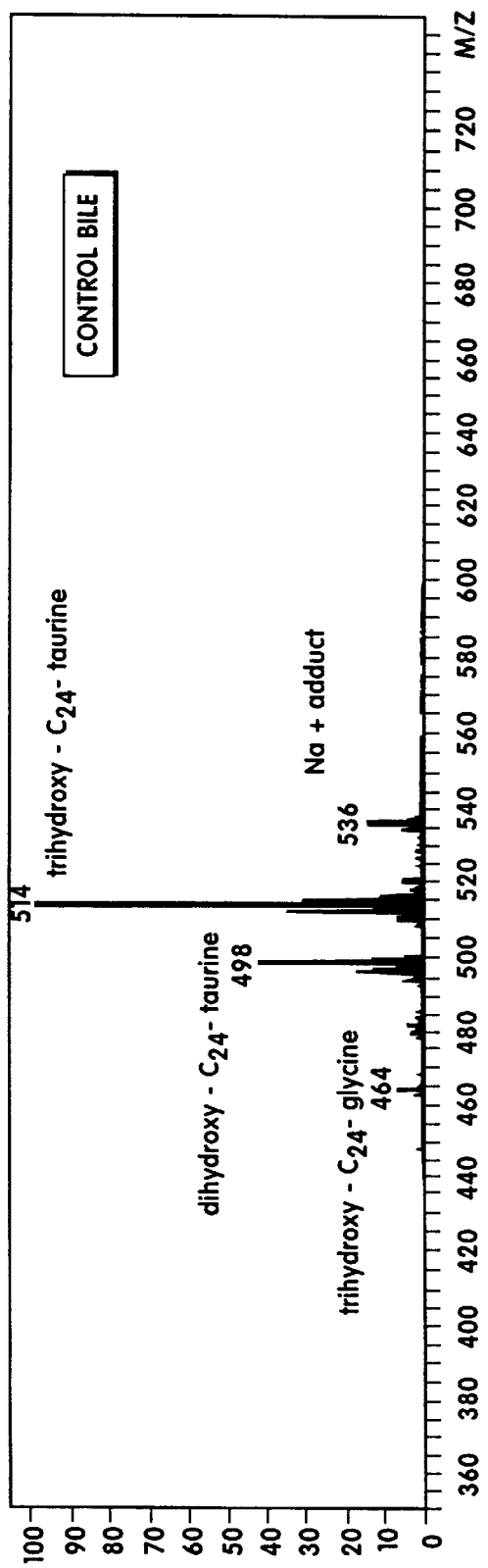
FIGS. 8A–8E show negative ion FAB-MS spectra of rat bile preinfusion (FIG. 8A), during UDCA infusion (FIG. 8B), during UDCA 3-S infusion (FIG. 8C), during UDCA 7-S infusion (FIG. 8D) and during UDCA-DS infusion (FIG. 8E).
Figure 8B:
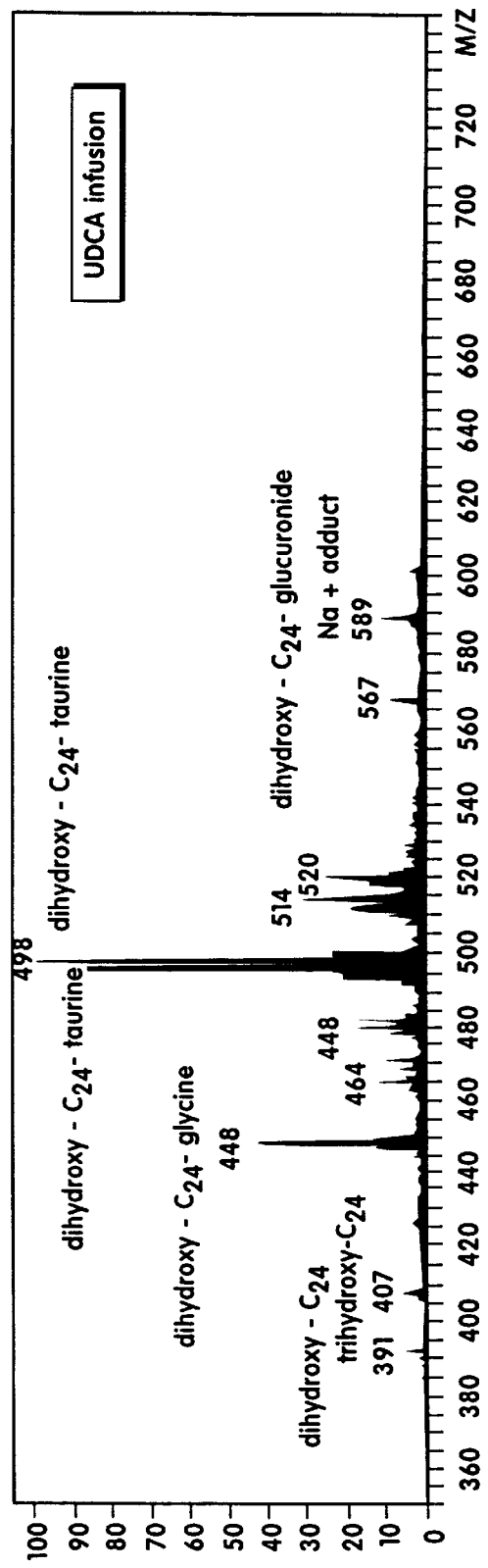

Negative ion FAB-MS spectra of the pooled rat bile collected before (basal period) and during infusion of unconjugated UDCA are shown in FIGS. 8A and 8B. The ions of m/z 514 and m/z 498 in the basal bile samples represent the taurine conjugates of trihydroxy- and dihydroxy-cholanoates respectively and represent primary bile acids which are major species in rat bile. During infusion of UDCA, the predominant ions in the spectrum became m/z 498 and m/z 448 indicating that infused UDCA was almost exclusively conjugated with taurine and glycine. The ion at m/z 471 indicates a dihydroxycholanoate (UDCA) sulfate while those at m/z 567 and m/z 589 (sodium adduct) represent flucuronide conjugates of UDCA.

During infusion of UDCA-7S, the predominant ions in the spectrum (FIG. 8D) were m/z 471 and its sodium adduct m/z 493, and these ions represent unchanged UDCA-7S. No other significant ions were present to indicate further metabolic transformation of UDCA-7S.

Figure 8C:
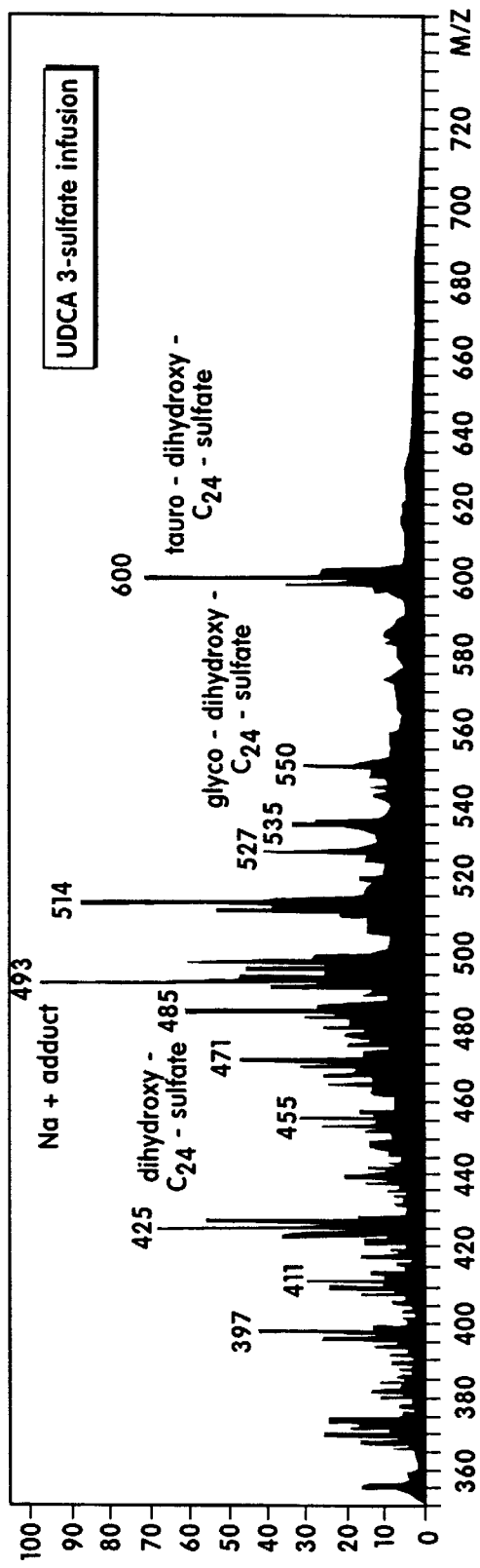
Figure 8D:
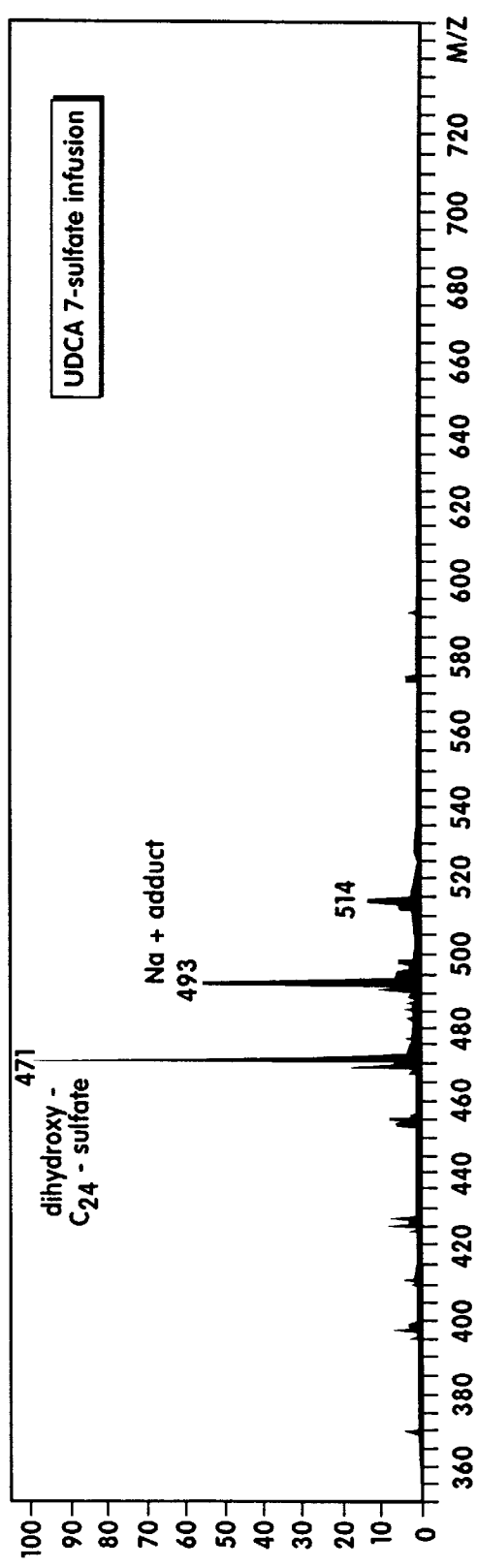

During infusion of UDCA-3S, ions at m/z 471 and m/z 493 (sodium adduct) confirmed biliary secretion of the unchanged bile acid and the ions at m/z 550 and mlz 600 reflect amidation with glycine and taurine (FIG. 8C).

Figure 8E:
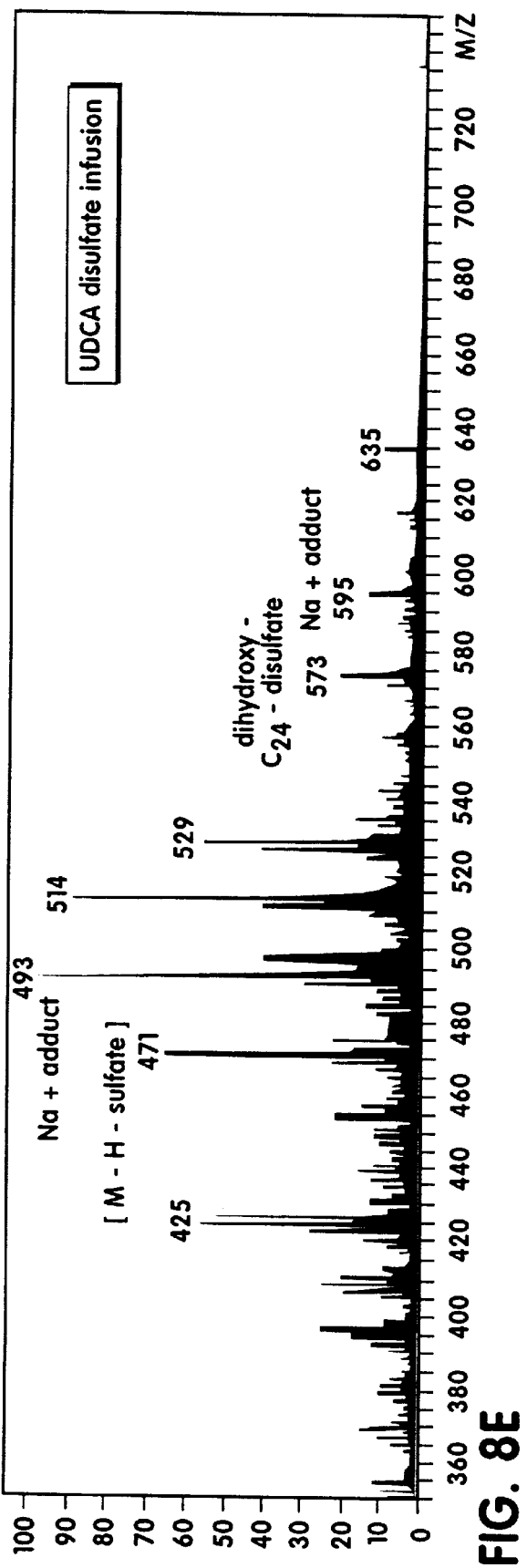

During infusion of UDCA-DS, the predominant ions were m/z 471 and m/z 493 (sodium adduct) and m/z 573. The ion of m/z 573 represents UDCA-DS, and m/z 471 and m/z 493 are fragment ions. No other ions were present to suggest further metabolic transformation of UDCA-DS (FIG. 8E).

GC-MS Analysis of Biliary Bile Acids

Table 5 summarizes the relative percentage composition of individual bile acids in bile following infusion of UDCA and the various sulfate conjugates. In the basal state, cholic acid, α-muricholic and β-muricholic acids were major bile acids of rat bile. During infusion of all of the compounds, UDCA became the predominant biliary bile acid and the percentage composition was similar among all groups, indicating that all of the sulfated bile acids were taken up by the liver and efficiently secreted into bile.

There was no evidence to support any biotransformation including amidation of the C-7 sulfate and the disulfate esters of UDCA, however both unconjugated UDCA and UDCA-3S were metabolized by further hydroxylation, most probably in the side-chain, however the exact structure of this hydroxlated metabolite remains to be definitively established.

Separation of bile acid conjugates secreted in bile during infusion of UDCA-3S indicated that equal proportions (25%) of the infused bile acid were recovered as taurine and glycine conjugates, while UDCA was almost exclusively conjugated with taurine and glycine. Because of the lack of biotransformation of UDCA-7S and UDCA-DS, confirmed by FAB-MS, further conjugate separation studies were deemed to be unnecessary.

Urinary Bile Acid Analysis

Negative ion FAB-MS analysis of all urine samples indicate that the sulfate esters of UDCA were all excreted in urine, and this was confirmed by GC-MS analysis. Quantitatively, however, the relative proportion of UDCA sulfate excreted in urine was small compared with the biliary excretion which was the major route of elimination. When UDCA was infused negligible proportions (0.01%) of the total dose administered appeared in the urine. For UDCA-3-sulfate, UDCA-7-sulfate and UDCA-disulfate, the corresponding proportions of the administered doses appearing in urine were 2.8%, 0.9% and 2.2% respectively.

DISCUSSION

The results presented above demonstrate that, like UDCA, all of the sulfate conjugates are markedly choleretic and increase bile acid secretion. The order of maximum bile-flow for the individual bile acids was UDCA-DS=UDCA-7S>UDCA>UDCA-3S, and was not directly related to their relative hydrophobic/hydrophilic nature as determined from the HPLC retention indices.

The presence of a sulfate moiety in the C-7 position of the bile acid nucleus results in a significantly higher bile-flow than that induced by UDCA, while the C-3 sulfate, although being choleretic, was less effective in stimulating bile-flow than unconjugated UDCA. These differences might be explained by the fact that significant amidation of the C-3 sulfate takes place during first-pass hepatic clearance, whereas a sulfate moiety at the position C-7 prevents biotransformation. It is possible that the amidated sulfates have lower choleretic properties. Interestingly the relative proportions of UDCA appearing in the bile were similar for all of the bile acids examined even though there were significant differences in bile-flow among these compounds.

With regard to cholesterol and phospholipid secretion a clear trend was evident. The bile acids that were the most polar (evidenced by their HPLC retention indices) were found to cause a significant decrease in biliary cholesterol and phospholipid output. This relationship between bile acid hydrophobicity/hydrophilicity and cholesterol and phospholipid secretion is most probably associated with the detergenicity of the molecule, i.e., the less detergent and highly polar bile acid sulfates are less membrane damaging than the more hydrophobic bile acids.

The combined effects of a lower cholesterol and phospholipid secretion and greater hypercholeresis induced by the highly hydrophilic 3-sulfate and 3,7-disulfate conjugates of UDCA compared with unconjugated UDCA would suggest that these particular bile acid sulfates might be more efficacious agents for the treatment of cholestatic liver disease.

Marked differences in hepatic biotransformation of the individual UDCA sulfates were observed. For example, substitution of a sulfate moiety at position C-7 in the nucleus hindered hepatic biotransformation so that UDCA-7-sulfate and UDCA-disulfate were both secreted into bile unchanged. This was not the case for the C-3 sulfate of UDCA, which was secreted into bile to a limited extent unchanged, but also underwent appreciable amidation with taurine and glycine and further hydroxylation, most probably in the side-chain. Unconjugated UDCA on the other hand was mainly conjugated with taurine, and to a lesser extent was converted to glycine, sulfate and flucuronide conjugates before biliary secretion.

Negligible amounts of UDCA sulfates were excreted in the urine even following infusion of relatively high concentrations. This was particularly surprising when one considers that the majority of urinary bile acids are sulfate conjugates. The lack of biliary bile acid sulfates in patients with cholestatic liver disease and the finding of high proportions and high concentrations of sulfated urinary bile acids can therefore only be explained by renal sulfation, and not hepatic sulfation of bile acids. These observations clearly demonstrate that sulfated bile acids are readily taken up by the liver and transported into bile, and therefore, would not appear to support the generally held belief that hepatic sulfation is an important metabolic pathway in cholestasis. In this respect, the kidney may be an important metabolic organ in protecting the liver from the toxicity of bile acids during cholestasis.

The rat is a species that significantly 6β-hydroxylates bile acids, and 6β-hydroxylation of CDCA and UDCA has been shown to occur. In this study, significant amounts of hydroxylated products of UDCA, such as muricholic acid isomers, could not be detected. It has been reported that taurochenodeoxycholic acid disulfates and glycochenodeoxycholic acid disulfates were metabolized by 90% to 3α, 7α-disulfate, 6β-hydroxy 5β-cholanoic acid (3α, 7α-disulfate of α-muricholic acid) rats whith a bile fistula. In the experiments conducted with regard to the invention, neither UDCA-7S nor UDCA-disulfate were hydroxylated. These experiments strongly suggest that the presence of the sulfate group prevents hepatic biotransformation of the nucleus. However, it might be possible that the enzyme responsible for hydroxylation preferentially acts upon the amidated bile acids as substrates.

It is thought that conjugation of bile acids with taurine depends on the substrate affinity of the enzyme (bile acid CoA:glycine/taurine-N-acyl-transferase) and the supply of taurine in the liver. Our results of FAB-MS and GC-MS showing that UDCA-3S was amidated partially with taurine and glycine, indicates the sulfate ester has less affinity for the enzyme compared with the nonsulfate bile acid. The observation that UDCA-7S and UDCA-DS were not amidated with taurine or glycine indicates that the presence of a 7β-sulfate moiety hinders the enzyme activity.

TABLE 1

Mass and Percent Composition of the Principal Bile Acids in Jejunum From Control Rats and After
Oral Administration of UDCA, UDCA 3-Sulfate, UDCA 7-Sulfate, or UDCA 3,7-Disulfate, Determined by GC-MS

|  | CONTROL | | UDCA | | UDCA 3-SULFATE | | UDCA 7-SULFATE | | UDCA 3,7-SULFATE | |
| --- | --- | --- | --- | --- | --- | --- | --- | --- | --- | --- |
|  | MASS (mg) | PERCENT (%) | MASS (mg) | PERCENT (%) | MASS (mg) | PERCENT (%) | MASS (mg) | PERCENT (%) | MASS (mg) | PERCENT (%) |
| LITHOCHOLIC ACID | 0.02 ± 0.01 | 0.2 ± 0.1 | 0.26 ± 0.01 | 1.0 ± 0.1 | 0.07 ± 0.01 | 0.3 ± 0.1 | 0.01 ± 0.01 | 0.1 ± 0.1 | ND | 0 |
| DEOXYCHOLIC ACID | 0.50 ± 0.03 | 4.8 ± 1.1 | 1.56 ± 0.18 | 5.6 ± 0.3 | 1.96 ± 0.68 | 8.4 ± 1.5 | 0.76 ± 0.08 | 3.3 ± 0.1 | 0.5 ± 0.05 | 5.2 ± 0.3 |
| CHENODEOOXYCHOLIC ACID | 0.25 ± 0.05 | | 0.98 ± 0.06 | | 0.43 ± 0.10 | | 0.26 ± 0.06 | | 0.12 ± 0.04 | |
| α-MURICHOLIC ACID | 1.48 ± 0.24 | | 0.75 ± 0.02 | | 0.18 ± 0.02 | | 0.04 ± 0.01 | | ND | |
| CHOLIC ACID | 6.82 ± 1.10 | 48.5 ± 2.9 | 4.68 ± 0.65 | 16.8 ± 1.3 | 8.49 ± 1.22 | 37.7 ± 0.9 | 15.78 ± 1.30 | 69.0 ± 0.6 | 6.78 ± 1.03 | 66.0 ± 1.3 |
| UDCA | 0.03 ± 0.01 | 0.3 ± 0.2 | 9.95 ± 0.49 | 35.9 ± 0.4 | 3.67 ± 0.45 | 16.4 ± 0.5 | 1.09 ± 0.34 | 4.7 ± 1.3 | 0.21 ± 0.07 | 2.0 ± 0.4 |
| $\Delta^{22}$-UDCA | ND | 0 | 4.00 ± 0.05 | 14.5 ± 0.7 | 2.04 ± 0.08 | 9.2 ± 1.0 | 0.70 ± 0.05 | 3.1 ± 0.1 | 0.21 ± 0.03 | 2.1 ± 0.1 |
| β-MURICHOLIC ACID | 0.64 ± 0.18 | | 4.12 ± 0.25 | | 3.02 ± 0.80 | | 2.21 ± 0.17 | | 1.70 ± 0.14 | |
| $\Delta^{22}$-β-MURICHOLIC ACID | 3.44 ± 0.57 | | 0.85 ± 0.01 | | 2.09 ± 0.16 | | 1.49 ± 0.22 | | 0.34 ± 0.09 | |
| ω-MURICHOLIC ACID | 0.10 ± 0.01 | | 0.31 ± 0.01 | | 0.37 ± 0.03 | | 0.31 ± 0.04 | | 0.24 ± 0.02 | |
| $\Delta^{22}$-ω-MURICHOLIC ACID | 0.56 ± 0.08 | | 0.30 ± 0.01 | | 0.24 ± 0.01 | | 0.26 ± 0.01 | | 0.12 ± 0.01 | |
| TOTAL | 4.04 ± 2.40 | | 27.77 ± 1.69 | | 22.57 ± 3.53 | | 22.91 ± 2.11 | | 10.24 ± 1.37 | |

NOTE: RESULTS ARE EXPRESSED AS MEAN ± SEM
ND: NOT DETECTED

TABLE 2

Mass and Percent Composition of the Principal Bile Acids in Colon From Control Rats and After
Oral Administration of UDCA, UDCA 3-Sulfate, UDCA 7-Sulfate, or UDCA 3,7-Disulfate, Determined by GC-MS

|  | CONTROL | | UDCA | | UDCA 3-SULFATE | | UDCA 7-SULFATE | | UDCA 3,7-SULFATE | |
| --- | --- | --- | --- | --- | --- | --- | --- | --- | --- | --- |
|  | MASS (mg) | PERCENT (%) | MASS (mg) | PERCENT (%) | MASS (mg) | PERCENT (%) | MASS (mg) | PERCENT (%) | MASS (mg) | PERCENT (%) |
| LITHOCHOLIC ACID | 0.08 ± 0.02 | 3.4 ± 0.2 | 0.97 ± 0.43 | 32.0 ± 0.8 | 0.61 ± 0.19 | 18.4 ± 7.2 | 0.04 ± 0.02 | 1.3 ± 0.3 | 0.02 ± 0.10 | 1.8 ± 0.6 |
| DEOXYCHOLIC ACID | 0.94 ± 0.34 | 32.3 ± 0.8 | 0.31 ± 0.13 | 10.4 ± 0.9 | .58 ± 0.07 | 17.4 ± 3.3 | 0.36 ± 0.16 | 11.4 ± 2.1 | 0.31 ± 0.04 | 27.2 ± 6.0 |
| CHENODEOOXYCHOLIC ACID | 0.03 ± 0.01 | | 0.05 ± 0.03 | | 0.06 ± 0.01 | | 0.06 ± 0.03 | | 0.07 ± 0.05 | |
| α-MURICHOLIC ACID | 0.15 ± 0.05 | | 0.01 ± 0.01 | | 0.02 ± 0.01 | | 0.03 ± 0.02 | | 0.03 ± 0.01 | |
| CHOLIC ACID | 0.47 ± 0.12 | 15.5 ± 1.7 | 0.24 ± 0.07 | 8.9 ± 2.8 | 0.44 ± .012 | 13.8 ± 5.3 | 0.09 ± 0.09 | 2.5 ± 2.0 | 0.23 ± 0.15 | 26.3 ± 9.8 |
| UDCA | 0.02 ± 0.01 | 0.6 ± 0.2 | 0.31 ± 0.26 | 8.3 ± 3.4 | 0.05 ± 0.02 | 1.5 ± 0.2 | 1.28 ± 0.38 | 44.0 ± 9.5 | 0.20 ± 0.17 | 14.7 ± 11.0 |
| $\Delta^{22}$-UDCA | ND | 0 | 0.02 ± 0.01 | 0.4 ± 0.1 | 0.01 ± 0.01 | 0.2 ± 0.1 | ND | 0 | ND | 0 |
| β-MURICHOLIC ACID | 0.31 ± 0.06 | | 0.13 ± 0.06 | | 0.20 ± 0.03 | | 0.06 ± 0.04 | | 0.06 ± 0.20 | |
| $\Delta^{22}$-β-MURICHOLIC ACID | 0.04 ± 0.01 | | ND | | 0.01 ± 0.01 | | 0.03 ± 0.01 | | 0.01 ± 0.01 | |
| ω-MURICHOLIC ACID | 0.82 ± 0.30 | | 0.83 ± 0.35 | | 1.67 ± 0.34 | | 0.88 ± 0.30 | | 0.24 ± 0.10 | |
| $\Delta^{22}$-ω-MURICHOLIC ACID | 0.24 ± 0.10 | | 0.19 ± 0.08 | | 0.44 ± 0.08 | | 0.15 ± 0.02 | | 0.06 ± 0.30 | |
| TOTAL | 3.17 ± 0.51 | | 3.04 ± 1.37 | | 4.07 ± 0.71 | | 2.98 ± 0.85 | | 1.22 ± 0.25 | |

NOTE: RESULTS ARE EXPRESSED AS MEAN ± SEM
ND: NOT DETECTED

TABLE 3

Mass and Percent Composition of the Principal Bile Acids in Liver From Control Rats and After
Oral Administration of UDCA, UDCA 3-Sulfate, UDCA 7-Sulfate, or UDCA 3,7-Disulfate, Determined by GC-MS

| | CONTROL | | UDCA | | UDCA 3-SULFATE | | UDCA 7-SULFATE | | UDCA 3,7-SULFATE | |
|---|---|---|---|---|---|---|---|---|---|---|
| | CONCENTRATION (nmol/g) | PERCENT (%) | CONCENTRATION (nmol/g) | PERCENT (%) | CONCENTRATION (nmol/g) | PERCENT (%) | CONCENTRATION (nmol/g) | PERCENT (%) | CONCENTRATION (nmol/g) | PERCENT (%) |
| LITHOCHOLIC ACID | 4.6 | 1.1 | 8.0 | 2.4 | 3.2 | 0.9 | 3.2 | 1.0 | 2.2 | 0.8 |
| DEOXYCHOLIC ACID | 29.0 | 6.7 | 22.5 | 6.8 | 52.6 | 14.5 | 14.9 | 4.5 | 17.3 | 6.1 |
| CHENODEOOXYCHOLIC ACID | 17.2 | 4.0 | 12.4 | 3.7 | 9.2 | 2.5 | 6.4 | 1.9 | 0.7 | 0.2 |
| α-MURICHOLIC ACID | 39.7 | 9.1 | 16.1 | 4.8 | 6.0 | 1.6 | 0.4 | 0.1 | 6.5 | 2.3 |
| CHOLIC ACID | 157.5 | 36.2 | 42.3 | 12.7 | 86.6 | 23.9 | 186.1 | 56.0 | 163.2 | 57.7 |
| UDCA | 12.0 | 2.8 | 99.6 | 30.0 | 56.6 | 15.6 | 6.1 | 1.8 | 4.9 | 1.7 |
| $\Delta^{22}$-UDCA | ND | 0.0 | 37.4 | 11.3 | 31.3 | 8.6 | 8.7 | 2.6 | 5.8 | 2.0 |
| β-MURICHOLIC ACID | 45.8 | 10.5 | 60.6 | 18.3 | 65.4 | 18.1 | 36.1 | 10.8 | 50.1 | 17.7 |
| $\Delta^{22}$-β-MURICHOLIC ACID | 129.1 | 29.7 | 20.9 | 6.3 | 36.3 | 10.0 | 59.8 | 18.0 | 23.0 | 8.1 |
| ω-MURICHOLIC ACID | ND | 0.0 | 6.3 | 1.9 | 8.1 | 2.2 | 4.0 | 1.2 | 5.0 | 1.8 |
| $\Delta^{22}$-ω-MURICHOLIC ACID | ND | 0.0 | 4.8 | 1.4 | 6.3 | 1.7 | 6.6 | 2.0 | 4.0 | 1.4 |
| TOTAL | 434.9 | | 331.8 | | 361.7 | | 332.3 | | 282.7 | |

NOTE: RESULTS ARE EXPRESSED AS MEAN ± SEM
ND: NOT DETECTED

TABLE 4

Physiological effects of infusion of UDCA and its sulfate conjugates

| | UDCA | UDCA-7S | UDCA-3S | UDCA-DS |
|---|---|---|---|---|
| Bile flow: (μl/min/g liver) | | | | |
| Basal | 1.97 ± 0.05 | 1.95 ± 0.08 | 1.85 ± 0.06 | 2.06 ± 0.07 |
| Maximum | 4.88 ± 0.16 | 5.83 ± 0.31 | 3.34 ± 0.13 | 5.92 ± 0.21 |
| Bile salt output: (nmol/min/g liver) | | | | |
| Basal | 47.30 ± 4.30 | 34.60 ± 4.40 | 39.60 ± 3.80 | 40.20 ± 5.50 |
| Maximum | 145.10 ± 17.30 | 255.40 ± 18.20 | 138.90 ± 11.80 | 222.40 ± 24.30 |
| Cholesterol output: (nmol/min/g liver) | | | | |
| Basal | 1.46 ± 0.10 | 1.42 ± 0.16 | 1.28 ± 0.05 | 1.52 ± 0.12 |
| Maximal change | 1.88 ± 0.19 | 1.76 ± 0.23 | 0.40 ± 0.02 | 0.37 ± 0.07 |
| Phospholipid output: (nmol/min/g liver) | | | | |
| Basal | 10.30 ± 0.70 | 9.00 ± 1.00 | 9.60 ± 0.80 | 9.80 ± 0.70 |
| Maximal change | 17.20 ± 1.90 | 15.00 ± 1.70 | 4.00 ± 0.50 | 2.50 ± 0.30 |

Values are expressed as mean ± SEM tor six animals in each group.

TABLE 5

Relative % composition of individual bile acids secreted in bile
during i.v. infusion of UDCA and the sulfate conjugates of UDCA

| Time (min) | DCA | CDCA | α-MCA | CA | UDCA | β-MCA | MCA | others |
|---|---|---|---|---|---|---|---|---|
| UDCA infusion: | | | | | | | | |
| Basal | 2.0 | 5.4 | 8.9 | 76.5 | 3.2 | 26.9 | 1.5 | nd |
| 20–30 mins | 1.0 | 3.0 | 4.3 | 49.0 | 51.9 | 17.2 | 1.0 | 14.6 |
| 50–60 mins | 0.5 | 2.5 | 3.9 | 21.4 | 65.9 | 12.6 | 0.5 | 13.7 |
| 80–90 mins | 0.7 | 1.5 | 6.4 | 9.8 | 79.5 | 9.9 | nd | 11.9 |
| UDCA-7S infusion: | | | | | | | | |
| Basal | 5.7 | 5.3 | 7.2 | 58.3 | 1.4 | 18.5 | 3.6 | nd |
| 20–30 mins | 2.3 | 1.7 | 2.5 | 20.2 | 61.3 | 10.7 | 1.3 | nd |

TABLE 5-continued

Relative % composition of individual bile acids secreted in bile
during i.v. infusion of UDCA and the sulfate conjugates of UDCA

| Time (min) | DCA | CDCA | α-MCA | CA | UDCA | β-MCA | MCA | others |
|---|---|---|---|---|---|---|---|---|
| 50–60 mins | 0.7 | 0.6 | 0.9 | 7.7 | 83.6 | 5.9 | 0.6 | nd |
| 80–90 mins | 1.2 | 0.7 | 1.3 | 9.9 | 78.8 | 7.4 | 0.8 | nd |
| UDCA-3S infusion: | | | | | | | | |
| Basal | 2.2 | 4.0 | 10.8 | 57.4 | 2.0 | 20.6 | 3.0 | nd |
| 20–30 mins | 2.5 | 4.6 | 6.2 | 36.0 | 33.3 | 12.4 | 4.9 | 5.2 |
| 50–60 mins | 1.0 | 1.9 | 2.7 | 14.9 | 70.6 | 7.4 | 1.5 | 11.5 |
| 80–90 mins | 1.3 | 2.5 | 3.0 | 18.2 | 67.7 | 5.2 | 2.0 | 11.2 |
| UDCA-DS infusion: | | | | | | | | |
| Basal | 4.2 | 6.3 | 9.1 | 56.7 | 1.4 | 18.0 | 4.3 | nd |
| 20–30 mins | 2.1 | 2.5 | 3.4 | 24.5 | 54.6 | 9.7 | 3.2 | nd |
| 50–60 mins | 1.2 | 0.7 | 2.2 | 15.3 | 70.7 | 6.7 | 2.2 | nd |
| 80–90 mins | nd | 0.9 | 1.6 | 10.6 | 79.1 | 6.5 | 1.4 | nd |

Although several particular aspects of the invention have been discussed in detail above, the scope of the invention is not limited to these aspects, and instead, is to be determined by the following claims.

What is claimed is:

1. A pharmacologically acceptable composition for inhibiting or treating a liver disease or an inflammatory condition of the gastrointestinal tract in a mammal, comprising:
   a sulfate of 3 alpha, 7 beta-dihydroxy-5 beta-cholan-24-oic acid (UDCA) or a salt thereof; and
   a pharmacologically acceptable carrier,
   said sulfate present in an amount effective to inhibit or treat said liver disease or inflammatory condition of the gastrointestinal tract in a mammal.

2. The pharmacologically acceptable composition of claim 1 wherein said sulfate is selected from the group consisting of UDCA-3-sulfate, UDCA-7-sulfate, UDCA-3,7-disulfate, glyco-UDCA-3-sulfate, glyco-UDCA-7-sulfate, glyco-UDCA-3,7-disulfate, tauro-UDCA-3-sulfate, tauro-UDCA-7-sulfate, tauro-UDCA-3,7-disulfate and combinations thereof.

3. The pharmacologically acceptable composition of claim 1 wherein said sulfate is selected from the group consisting of UDCA-3-sulfate, UDCA-7-sulfate, UDCA-3,7-disulfate and combinations thereof.

4. The pharmacologically acceptable composition of claim 1 wherein said sulfate is selected from the group consisting of UDCA-7-sulfate, UDCA-3,7-disulfate and combinations thereof.

5. The pharmacologically acceptable composition of claim 1 wherein said sulfate is present in an amount effective to inhibit or treat an inflammatory condition of the gastrointestinal tract.

6. The pharmacologically acceptable composition of claim 5 wherein said sulfate is present in an amount effective to inhibit or treat an inflammatory condition of the small intestine, an inflammatory condition of the large intestine and combinations thereof.

7. The pharmacologically acceptable composition of claim 5 wherein said sulfate is present in an amount effective to inhibit or treat an inflammatory condition selected from the group consisting of colon cancer, rectum cancer, a neoplasm of the colon, a neoplasm of the rectum, carcinogenesis of the colon, carcinogenesis of the rectum, ulcerative colitis, an adenomatous polyp, familial polyposis and combinations thereof.

8. The pharmacologically acceptable composition of claim 1 wherein said sulfate is present in an amount effective to inhibit or treat an inflammatory condition of the liver.

9. The pharmacologically acceptable composition of claim 8 formulated for intravenous administration.

10. The pharmacologically acceptable composition of claim 1 wherein said sulfate is present in an amount effective to deliver UDCA to the large intestine of a mammal.

11. The pharmacologically acceptable composition of claim 10 wherein said sulfate includes a sulfate moiety on the C-7 carbon, said sulfate present in an amount effective to improve delivery of UDCA to the large intestine of a mammal, relative to delivery of UDCA to the large intestine by UDCA or a sulfate of UDCA without a sulfate moiety on the C-7 carbon.

12. The pharmacologically acceptable composition of claim 1 wherein said sulfate is present in an amount effective to inhibit the intestinal absorption of UDCA.

13. The pharmacologically acceptable composition of claim 1 wherein said sulfate is present in an amount effective to inhibit the intestinal transformation of UDCA and its metabolites.

14. The pharmacologically acceptable composition of claim 13 wherein said sulfate is present in an amount effective to inhibit the intestinal transformation of UDCA and its metabolites by bacterial degradation.

15. The pharmacologically acceptable composition of claim 14 wherein said sulfate is present in an amount effective to inhibit the intestinal transformation of UDCA and its metabolites by 7 alpha-dehydroxylation.

16. The pharmacologically acceptable composition of claim 1 wherein said sulfate includes a sulfate moiety on the C-7 carbon, said sulfate present in an amount effective to decrease the amount of lithocholic acid or a salt thereof and deoxycholic acid or a salt thereof in the colon.

17. The pharmacologically acceptable composition of claim 1 wherein said sulfate includes a sulfate moiety on the C-7 carbon, said sulfate present in an amount effective to deliver UDCA to the colon without substantially increasing the ratio of lithocholic acid or a salt thereof to deoxycholic acid or a salt thereof in the colon.

18. The pharmacologically acceptable composition of claim 1 wherein said sulfate is present in an amount effective to improve serum biochemistries of liver disease and liver function.

19. The pharmacologically acceptable composition of claim 18 wherein said sulfate is present in an amount effective to improve serum concentrations of an enzyme selected from the group consisting of alanine aminotransferase, aspartate aminotransferase, alkaline phosphatase, gamma-glutamyltranspeptidase and combinations thereof.

20. The pharmacologically acceptable composition of claim 1 wherein said sulfate is present in an amount effective to increase bile flow.

21. The pharmacologically acceptable composition of claim 1 wherein said sulfate is present in an amount effective to decrease biliary secretion of a lipid selected from the group consisting of phospholipid, cholesterol and combinations thereof.

22. The pharmacologically acceptable composition of claim 1 formulated for oral, local or intravenous administration.

* * * * *